(12) United States Patent
Flores, II et al.

(10) Patent No.: US 11,207,054 B2
(45) Date of Patent: Dec. 28, 2021

(54) TRANSCRANIAL DOPPLER PROBE

(71) Applicant: NovaSignal Corp., Los Angeles, CA (US)

(72) Inventors: Roman Flores, II, Los Angeles, CA (US); Matthew Hutter, Los Angeles, CA (US); Gerard Salinas, Los Angeles, CA (US); Michael Costa, Los Angeles, CA (US); Matthew Sylvester, Los Angeles, CA (US); Robert Hamilton, Los Angeles, CA (US); Corey Thibeault, Los Angeles, CA (US); Leo Petrossian, Los Angeles, CA (US); Aaron Green, Los Angeles, CA (US); Shankar Radhakrishnan, Los Angeles, CA (US)

(73) Assignee: NovaSignal Corp., Los Angeles, CA (US)

( * ) Notice: Subject to any disclaimer, the term of this patent is extended or adjusted under 35 U.S.C. 154(b) by 1416 days.

(21) Appl. No.: 15/187,397

(22) Filed: Jun. 20, 2016

(65) Prior Publication Data

US 2016/0367217 A1 Dec. 22, 2016

Related U.S. Application Data

(60) Provisional application No. 62/181,862, filed on Jun. 19, 2015, provisional application No. 62/181,859, (Continued)

(51) Int. Cl.
*A61B 8/08* (2006.01)
*A61B 8/00* (2006.01)

(52) U.S. Cl.
CPC ............ *A61B 8/488* (2013.01); *A61B 8/0808* (2013.01); *A61B 8/4218* (2013.01); (Continued)

(58) Field of Classification Search
None
See application file for complete search history.

(56) References Cited

U.S. PATENT DOCUMENTS 3,841,308 A 10/1974 Tate
3,872,858 A 3/1975 Hudson et al.
(Continued)

FOREIGN PATENT DOCUMENTS

CN 104605889 A 5/2015
EP 0 403 807 A2 12/1990
(Continued)

OTHER PUBLICATIONS

International Search Report and Written Opinion dated May 4, 2017, from application No. PCT/US2017/012395.
(Continued)

*Primary Examiner* — Joanne M Hoffman
(74) *Attorney, Agent, or Firm* — Foley & Lardner LLP

(57) ABSTRACT

According to various embodiments, there is provided a headset mountable on a head, the headset including a probe for emitting energy into the head. The headset further includes a support structure coupled to the probe. The support structure includes translation actuators for translating the probe along two axes generally parallel to a surface of the head.

20 Claims, 13 Drawing Sheets

US 11,207,054 B2
Page 2

Related U.S. Application Data filed on Jun. 19, 2015, provisional application No. 62/347,527, filed on Jun. 8, 2016.

(52) U.S. Cl.
CPC .......... *A61B 8/4227* (2013.01); *A61B 8/4466* (2013.01); *A61B 8/54* (2013.01)

(56) References Cited

U.S. PATENT DOCUMENTS

| | | |
|---|---|---|
| 4,204,547 A | 5/1980 | Allocca |
| 4,205,687 A | 6/1980 | White et al. |
| 4,413,629 A | 11/1983 | Durley, III |
| 4,483,344 A | 11/1984 | Atkov et al. |
| 4,559,952 A | 12/1985 | Angelsen et al. |
| 4,759,374 A | 7/1988 | Kierney et al. |
| 4,815,705 A | 3/1989 | Kasugai et al. |
| 4,819,648 A | 4/1989 | Ko |
| 4,841,986 A | 6/1989 | Marchbanks |
| 4,930,513 A | 6/1990 | Mayo et al. |
| 4,951,653 A | 8/1990 | Fry et al. |
| 4,984,567 A | 1/1991 | Kageyama et al. |
| 5,040,540 A | 8/1991 | Sackner |
| 5,074,310 A | 12/1991 | Mick |
| 5,094,243 A | 3/1992 | Puy et al. |
| 5,156,152 A | 10/1992 | Yamazaki et al. |
| 5,197,019 A | 3/1993 | Delon-Martin et al. |
| 5,348,015 A | 9/1994 | Moehring et al. |
| 5,379,770 A | 1/1995 | Van Veen |
| 5,388,583 A | 2/1995 | Ragauskas et al. |
| 5,409,005 A * | 4/1995 | Bissonnette ......... A61B 8/0808 600/437 |
| 5,409,010 A | 4/1995 | Beach et al. |
| 5,411,028 A | 5/1995 | Bonnefous |
| 5,421,565 A | 6/1995 | Harkrader et al. |
| 5,514,146 A * | 5/1996 | Lam ..................... A61B 8/4209 606/130 |
| 5,522,392 A | 6/1996 | Suorsa et al. |
| 5,526,299 A | 6/1996 | Coifman et al. |
| 5,617,873 A | 4/1997 | Yost et al. |
| 5,840,018 A | 11/1998 | Michaeli |
| 5,860,929 A | 1/1999 | Rubin et al. |
| 5,871,445 A * | 2/1999 | Bucholz ............... A61B 5/0064 600/407 |
| 5,899,864 A | 5/1999 | Arenson et al. |
| 5,919,144 A | 7/1999 | Bridger et al. |
| 5,951,477 A | 9/1999 | Ragauskas et al. |
| 5,993,398 A | 11/1999 | Alperin |
| 6,027,454 A | 2/2000 | Low |
| 6,117,089 A | 9/2000 | Sinha |
| 6,120,446 A | 9/2000 | Ji et al. |
| 6,129,682 A | 10/2000 | Borchert et al. |
| 6,135,957 A | 10/2000 | Cohen-Bacrie et al. |
| 6,139,499 A | 10/2000 | Wilk |
| 6,200,267 B1 | 3/2001 | Burke |
| 6,231,509 B1 | 5/2001 | Johnson et al. |
| 6,261,231 B1 | 7/2001 | Damphousse et al. |
| 6,309,354 B1 | 10/2001 | Madsen et al. |
| 6,358,239 B1 | 3/2002 | Rake et al. |
| 6,364,869 B1 | 4/2002 | Bonaldo |
| 6,387,051 B1 | 5/2002 | Ragauskas et al. |
| 6,403,056 B1 | 6/2002 | Unger |
| 6,413,227 B1 | 7/2002 | Yost et al. |
| 6,423,003 B1 | 7/2002 | Ustuner et al. |
| 6,425,865 B1 | 7/2002 | Salcudean et al. |
| 6,454,715 B2 | 9/2002 | Teo |
| 6,488,717 B1 | 12/2002 | McColl et al. |
| 6,491,647 B1 | 12/2002 | Bridger et al. |
| 6,503,202 B1 | 1/2003 | Hossack et al. |
| 6,547,731 B1 | 4/2003 | Coleman et al. |
| 6,547,734 B2 | 4/2003 | Madsen et al. |
| 6,547,737 B2 | 4/2003 | Njemanze |
| 6,589,189 B2 | 7/2003 | Meyerson et al. |
| 6,618,493 B1 | 9/2003 | Torp et al. |
| 6,627,421 B1 | 9/2003 | Unger et al. |
| 6,653,825 B2 | 11/2003 | Munniksma |
| 6,656,125 B2 | 12/2003 | Misczynski et al. |
| 6,682,488 B2 | 1/2004 | Abend |
| 6,702,743 B2 | 3/2004 | Michaeli |
| 6,716,412 B2 | 4/2004 | Unger |
| 6,740,048 B2 | 5/2004 | Yost et al. |
| 6,746,422 B1 | 6/2004 | Noriega et al. |
| 6,875,176 B2 | 4/2005 | Mourad et al. |
| 6,887,199 B2 | 5/2005 | Bridger et al. |
| 6,955,648 B2 | 10/2005 | Mozayeni et al. |
| 7,122,007 B2 | 10/2006 | Querfurth |
| 7,128,713 B2 | 10/2006 | Moehring et al. |
| 7,147,605 B2 | 12/2006 | Ragauskas |
| 7,302,064 B2 | 11/2007 | Causevic et al. |
| 7,338,450 B2 | 3/2008 | Kristoffersen et al. |
| 7,403,805 B2 | 7/2008 | Abreu |
| 7,452,551 B1 | 11/2008 | Unger et al. |
| 7,534,209 B2 | 5/2009 | Abend et al. |
| 7,537,568 B2 | 5/2009 | Moehring |
| D594,127 S | 6/2009 | Causevic et al. |
| 7,547,283 B2 | 6/2009 | Mourad et al. |
| D603,051 S | 10/2009 | Causevic et al. |
| 7,674,229 B2 | 3/2010 | Hynynen et al. |
| 7,720,530 B2 | 5/2010 | Causevic |
| 7,771,358 B2 | 8/2010 | Moehring et al. |
| 7,815,574 B2 | 10/2010 | Mourad et al. |
| 7,854,701 B2 | 12/2010 | Stergiopoulos et al. |
| 7,857,763 B2 | 12/2010 | Tai |
| 7,904,144 B2 | 3/2011 | Causevic et al. |
| 7,912,269 B2 | 3/2011 | Ikeda et al. |
| 7,938,780 B2 | 5/2011 | Ragauskas et al. |
| 7,942,820 B2 | 5/2011 | Njemanze |
| D641,886 S | 7/2011 | Causevic et al. |
| 7,998,075 B2 | 8/2011 | Ragauskas et al. |
| RE42,803 E | 10/2011 | Lipson et al. |
| 8,036,856 B2 | 10/2011 | Pan et al. |
| 8,041,136 B2 | 10/2011 | Causevic |
| 8,062,224 B2 | 11/2011 | Ragauskas et al. |
| 8,075,488 B2 | 12/2011 | Burton |
| 8,109,880 B1 | 2/2012 | Pranevicius et al. |
| 8,162,837 B2 | 4/2012 | Moehring et al. |
| 8,206,303 B2 | 6/2012 | Ragauskas et al. |
| 8,211,023 B2 | 7/2012 | Swan et al. |
| 8,235,907 B2 | 8/2012 | Wilk et al. |
| 8,254,654 B2 | 8/2012 | Yen et al. |
| 8,265,291 B2 | 9/2012 | Bridger et al. |
| 8,353,853 B1 | 1/2013 | Kyle et al. |
| 8,364,254 B2 | 1/2013 | Jacquin et al. |
| 8,364,255 B2 | 1/2013 | Isenhart et al. |
| 8,366,627 B2 | 2/2013 | Kashif et al. |
| 8,391,948 B2 | 3/2013 | Causevic et al. |
| 8,394,024 B2 | 3/2013 | Miyama et al. |
| 8,394,025 B2 | 3/2013 | Ragauskas et al. |
| 8,414,539 B1 | 4/2013 | Kuracina et al. |
| 8,453,509 B2 | 6/2013 | Oberdorfer et al. |
| 8,473,024 B2 | 6/2013 | Causevic et al. |
| 8,603,014 B2 | 12/2013 | Alleman et al. |
| 8,613,714 B2 | 12/2013 | Alleman et al. |
| 8,622,912 B2 | 1/2014 | Chin et al. |
| 8,647,278 B2 | 2/2014 | Ji et al. |
| 8,706,205 B2 | 4/2014 | Shahaf et al. |
| 8,834,376 B2 | 9/2014 | Stergiopoulos et al. |
| 8,905,932 B2 | 12/2014 | Lovoi et al. |
| 8,926,515 B2 | 1/2015 | Ragauskas et al. |
| 8,998,818 B2 | 4/2015 | Pranevicius et al. |
| 9,005,126 B2 | 4/2015 | Beach et al. |
| 9,028,416 B2 | 5/2015 | De Viterbo |
| 9,042,201 B2 | 5/2015 | Tyler et al. |
| 9,066,679 B2 | 6/2015 | Beach et al. |
| 9,125,616 B2 | 9/2015 | Bredno et al. |
| 9,138,154 B2 | 9/2015 | Weinberg et al. |
| 9,192,359 B2 | 11/2015 | Flynn et al. |
| 9,196,037 B2 | 11/2015 | Jung |
| 9,630,028 B2 | 4/2017 | Browning et al. |
| RE46,614 E | 11/2017 | Lipson et al. |
| 2001/0053879 A1 | 12/2001 | Mills et al. |
| 2002/0103436 A1 | 8/2002 | Njemanze |
| 2003/0050607 A1 | 3/2003 | Gagnieux et al. |
| 2004/0267127 A1 | 12/2004 | Abend et al. |

(56) References Cited

U.S. PATENT DOCUMENTS

| | | |
|---|---|---|
| 2005/0004457 A1 | 1/2005 | Moilanen et al. |
| 2005/0004468 A1 | 1/2005 | Abend et al. |
| 2005/0015009 A1 | 1/2005 | Mourad et al. |
| 2005/0049515 A1 | 3/2005 | Misczynski et al. |
| 2005/0119573 A1 | 6/2005 | Vilenkin et al. |
| 2005/0124901 A1 | 6/2005 | Misczynski et al. |
| 2005/0147297 A1 | 7/2005 | McLaughlin et al. |
| 2005/0148895 A1 | 7/2005 | Misczynski et al. |
| 2006/0025801 A1 | 2/2006 | Lulo et al. |
| 2006/0030777 A1 | 2/2006 | Liang et al. |
| 2006/0049721 A1 | 3/2006 | Kuehnicke |
| 2006/0173307 A1 | 8/2006 | Amara et al. |
| 2006/0173337 A1 | 8/2006 | Chen et al. |
| 2006/0184070 A1 | 8/2006 | Hansmann et al. |
| 2006/0206037 A1 | 9/2006 | Braxton |
| 2006/0241462 A1 | 10/2006 | Chou et al. |
| 2007/0016046 A1 | 1/2007 | Mozayeni et al. |
| 2007/0016050 A1 | 1/2007 | Moehring et al. |
| 2007/0078345 A1 | 4/2007 | Mo et al. |
| 2007/0161891 A1 | 7/2007 | Moore et al. |
| 2007/0232918 A1 | 10/2007 | Taylor |
| 2007/0239019 A1 | 10/2007 | Richard et al. |
| 2007/0244398 A1 | 10/2007 | Lo et al. |
| 2008/0015478 A1 | 1/2008 | Bose |
| 2008/0058861 A1 | 3/2008 | Cooper et al. |
| 2008/0065099 A1 | 3/2008 | Cooper et al. |
| 2008/0132790 A1 | 6/2008 | Burton |
| 2008/0208060 A1 | 8/2008 | Murkin |
| 2008/0262350 A1 | 10/2008 | Unger |
| 2009/0062813 A1 | 3/2009 | Prisco et al. |
| 2009/0074151 A1 | 3/2009 | Henderson et al. |
| 2009/0198137 A1 | 8/2009 | Ragauskas et al. |
| 2009/0264786 A1 | 10/2009 | Jacquin |
| 2009/0275836 A1 | 11/2009 | Fujii et al. |
| 2009/0287084 A1 | 11/2009 | Ragauskas et al. |
| 2009/0306515 A1 | 12/2009 | Matsumura et al. |
| 2009/0326379 A1 | 12/2009 | Daigle et al. |
| 2010/0016707 A1 | 1/2010 | Amara et al. |
| 2010/0069757 A1 | 3/2010 | Yoshikawa et al. |
| 2010/0081893 A1 | 4/2010 | Jarvik et al. |
| 2010/0087728 A1 | 4/2010 | Jarvik et al. |
| 2010/0121192 A1 | 5/2010 | Nogata et al. |
| 2010/0125206 A1 | 5/2010 | Syme |
| 2010/0130866 A1 | 5/2010 | Main et al. |
| 2010/0160779 A1 | 6/2010 | Browning et al. |
| 2010/0274303 A1 | 10/2010 | Bukhman |
| 2010/0298821 A1 | 11/2010 | Garbagnati |
| 2011/0112426 A1 | 5/2011 | Causevic |
| 2011/0137182 A1 | 6/2011 | Bellezza et al. |
| 2011/0144518 A1 | 6/2011 | Causevic |
| 2011/0251489 A1* | 10/2011 | Zhang .................. A61B 8/4227 600/459 |
| 2011/0275936 A1 | 11/2011 | Cho et al. |
| 2011/0301461 A1 | 12/2011 | Anite |
| 2012/0108967 A1 | 5/2012 | Weng et al. |
| 2012/0108972 A1 | 5/2012 | Miyama et al. |
| 2012/0123272 A1 | 5/2012 | Lam et al. |
| 2012/0123590 A1 | 5/2012 | Halsmer |
| 2012/0153580 A1 | 6/2012 | Soma |
| 2012/0157840 A1 | 6/2012 | Syme |
| 2012/0165675 A1 | 6/2012 | Syme |
| 2012/0165676 A1 | 6/2012 | Njemanze |
| 2012/0226163 A1 | 9/2012 | Moehring et al. |
| 2012/0238875 A1 | 9/2012 | Savitsky et al. |
| 2013/0006106 A1 | 1/2013 | O'Reilly et al. |
| 2013/0018277 A1 | 1/2013 | Liu |
| 2013/0047452 A1 | 2/2013 | McMurtry et al. |
| 2013/0080127 A1 | 3/2013 | Shahaf et al. |
| 2013/0197401 A1 | 8/2013 | Sato et al. |
| 2013/0239687 A1 | 9/2013 | Nakabayashi |
| 2013/0274607 A1 | 10/2013 | Anand et al. |
| 2013/0289411 A1 | 10/2013 | Barnard et al. |
| 2014/0031690 A1 | 1/2014 | Toji et al. |
| 2014/0031693 A1 | 1/2014 | Solek |
| 2014/0081142 A1 | 3/2014 | Toma et al. |
| 2014/0081144 A1 | 3/2014 | Moehring et al. |
| 2014/0094701 A1 | 4/2014 | Kwartowitz et al. |
| 2014/0163328 A1 | 6/2014 | Geva et al. |
| 2014/0163379 A1 | 6/2014 | Bukhman |
| 2014/0171820 A1 | 6/2014 | Causevic |
| 2014/0194740 A1 | 7/2014 | Stein et al. |
| 2014/0276059 A1 | 9/2014 | Sheehan |
| 2014/0316269 A1 | 10/2014 | Zhang et al. |
| 2014/0323857 A1 | 10/2014 | Mourad et al. |
| 2014/0343431 A1 | 11/2014 | Vajinepalli et al. |
| 2015/0051489 A1 | 2/2015 | Caluser et al. |
| 2015/0065871 A1 | 3/2015 | Konofagou et al. |
| 2015/0065916 A1 | 3/2015 | Maguire et al. |
| 2015/0094582 A1 | 4/2015 | Tanaka et al. |
| 2015/0151142 A1 | 6/2015 | Tyler et al. |
| 2015/0157266 A1 | 6/2015 | Machon et al. |
| 2015/0190111 A1 | 7/2015 | Fry |
| 2015/0216500 A1 | 8/2015 | Mano et al. |
| 2015/0245771 A1 | 9/2015 | Wang et al. |
| 2015/0245776 A1 | 9/2015 | Hirohata et al. |
| 2015/0245820 A1 | 9/2015 | Tamada |
| 2015/0250446 A1 | 9/2015 | Kanayama |
| 2015/0250448 A1 | 9/2015 | Tamada |
| 2015/0297176 A1* | 10/2015 | Rincker ................. A61B 8/429 600/439 |
| 2015/0297177 A1 | 10/2015 | Boctor et al. |
| 2015/0302584 A1 | 10/2015 | Brauner et al. |
| 2015/0351718 A1 | 12/2015 | Vollmer et al. |
| 2015/0356734 A1 | 12/2015 | Ooga et al. |
| 2015/0359448 A1 | 12/2015 | Beach |
| 2016/0000367 A1 | 1/2016 | Lyon |
| 2016/0000411 A1 | 1/2016 | Raju et al. |
| 2016/0000516 A1 | 1/2016 | Cheng et al. |
| 2016/0030001 A1 | 2/2016 | Stein et al. |
| 2016/0094115 A1 | 3/2016 | Okawa et al. |
| 2016/0151618 A1 | 6/2016 | Powers et al. |
| 2016/0256130 A1 | 9/2016 | Hamilton et al. |
| 2016/0278736 A1 | 9/2016 | Hamilton et al. |
| 2016/0310006 A1 | 10/2016 | Aguero Villarreal et al. |
| 2016/0310023 A1 | 10/2016 | Chachisvilis et al. |
| 2016/0317129 A1 | 11/2016 | Seip et al. |
| 2016/0324585 A1 | 11/2016 | Noonan et al. |
| 2016/0367217 A1 | 12/2016 | Flores et al. |
| 2017/0119347 A1 | 5/2017 | Flores et al. |
| 2017/0188992 A1 | 7/2017 | O'Brien et al. |
| 2017/0188993 A1 | 7/2017 | Hamilton et al. |
| 2017/0188994 A1 | 7/2017 | Flores et al. |
| 2017/0196465 A1 | 7/2017 | Browning et al. |
| 2017/0307420 A1 | 10/2017 | Flores et al. |
| 2018/0021021 A1 | 1/2018 | Zwierstra et al. |
| 2018/0093077 A1 | 4/2018 | Harding et al. |
| 2018/0103927 A1 | 4/2018 | Chung et al. |
| 2018/0103928 A1 | 4/2018 | Costa et al. |
| 2018/0177487 A1 | 6/2018 | Deffieux et al. |
| 2018/0214124 A1 | 8/2018 | O'Brien et al. |
| 2018/0220991 A1 | 8/2018 | O'Brien et al. |
| 2019/0150895 A1 | 5/2019 | Tian et al. |

FOREIGN PATENT DOCUMENTS

| | | |
|---|---|---|
| EP | 1 750 804 | 2/2007 |
| EP | 2 034 901 | 3/2009 |
| EP | 2 111 787 | 10/2009 |
| EP | 2 858 619 | 4/2015 |
| FR | 2606625 A1 | 5/1988 |
| JP | S52-126979 A | 10/1977 |
| JP | H02-114008 | 4/1990 |
| JP | H05-143161 | 6/1993 |
| JP | H571763 U | 9/1993 |
| JP | 07-299066 A | 11/1995 |
| JP | 10-328189 A | 12/1998 |
| JP | 2003-225239 A | 8/2003 |
| JP | 2003-230558 A | 8/2003 |
| JP | 2003-245280 A | 9/2003 |
| JP | 2004-237082 A | 8/2004 |
| JP | 2006-025904 A | 2/2006 |
| JP | 2007-143704 A | 6/2007 |
| JP | 2010-500084 A | 1/2010 |
| JP | 2010-200844 A | 9/2010 |

(56) References Cited

FOREIGN PATENT DOCUMENTS

| JP | 2013-503681 A | 2/2013 |
|---|---|---|
| JP | 2015-533299 A | 11/2015 |
| WO | WO-95/02361 | 1/1995 |
| WO | WO-99/56625 | 11/1999 |
| WO | WO-2009/138882 A2 | 11/2009 |
| WO | WO-2010/042146 | 4/2010 |
| WO | WO-2013/155537 | 10/2013 |
| WO | WO-2014/070993 A1 | 5/2014 |
| WO | WO-2015/073903 A1 | 5/2015 |
| WO | WO-2015/092604 | 6/2015 |
| WO | WO-2016/001548 | 1/2016 |

OTHER PUBLICATIONS

M.H. Raibert et al., "Hybrid Position/Force Control of Manipulators", Journal of Dynamic Systems, Measurement, and Control, vol. 102, Jun. 1981, pp. 126-133, abstract.
Final Office Action dated Jun. 15, 2020, from U.S. Appl. No. 15/399,735.
Final Office Action dated Jun. 9, 2020, from U.S. Appl. No. 15/399,648.
Final Office Action dated Aug. 28, 2019, from U.S. Appl. No. 15/399,440.
Non-Final Office Action dated Oct. 1, 2019, from U.S. Appl. No. 15/399,735.
Chinese Office Action dated Aug. 18, 2020, from application No. 201780005508.2.
Chinese Office Action dated Jun. 30, 2020, from application No. 201780005447.X.
Final Office Action dated Sep. 18, 2020, from U.S. Appl. No. 15/399,710.
Non-Final Office Action dated Jul. 16, 2020, from U.S. Appl. No. 15/497,039.
Extended European Search Report dated Jul. 16, 2019, from application No. 17736353.8.
Extended European Search Report dated Jul. 19, 2019, from application No. 17736375.1.
Extended European Search Report dated Jul. 24, 2019, from application No. 17735919.7.
Final Office Action dated Aug. 2, 2019, from U.S. Appl. No. 15/399,648.
Ni, et al., "Serial Transcranial Doppler Sonography in Ischemic Strokes in Middle Cerebral Artery Territory", Journal of Neruoimaging, Oct. 1, 1994, pp. 232-236.
Non-Final Office Action dated Aug. 14, 2019, from U.S. Appl. No. 15/497,039.
International Search Report and Written Opinion dated Aug. 14, 2017, from international application No. PCT/US2017/029483.
Chinese Office Action dated Mar. 24, 2020, from application No. 201680034144.6.
Japanese Office Action dated Apr. 24, 2018, from application No. 2016-554529.
International Search Report and Written Opinion dated Oct. 13, 2016, from related international application No. PCT/US2016/038433.
Extended European Search Report dated Nov. 12, 2019, from application No. 17736371.0.
Extended European Search Report dated Nov. 21, 2019, from application No. 17790294.7.
Non-Final Office Action dated Dec. 11, 2019, from U.S. Appl. No. 15/399,710.
Non-Final Office Action dated Dec. 13, 2019, from U.S. Appl. No. 15/036,776.
Non-Final Office Action dated Nov. 19, 2019, from U.S. Appl. No. 15/399,648.
Notice of Allowance dated Dec. 9, 2019, from U.S. Appl. No. 15/399,440.
Aaslid, R., et al., "Noninvasive transcranial Doppler ultrasound recording of flow velocity in basal cerebral arteries", Journal of Neurosurgery, 1982, 57(6): p. 769-774.
Baldwin, K., et al., "Subpeak Regional Analysis of Intracranial Pressure Waveform Morphology based on Cerebrospinal Fluid Hydrodynamics in the Cerebral Aqueduct and Prepontine Cistern", 34th Annual International Conference of the IEEE EMBS, 2012, p. 3935-3938.
Bashford, G., et al.."Monitoring Cerebral Hemodynamics with Transcranial Doppler Ultrasound during Cognitive and Exercise Testing in Adults following Unilateral Stroke", 34th Annual International Conference of the IEEE EMBS, 2012, p. 2310-2313.
Chen, W., et al., "Intracranial Pressure Level Prediction in Traumatic Brain Injury by Extracting Features from Multiple Sources and Using Machine Learning Methods", 2010 IEEE International Conference on Bioinformatics and Biomedicine, 2010, p. 510-515.
Cheng, Y. & Zhao, R., "Self-training classifier via local learning regularization", Proceedings of the Eighth International Conference on Machine Learning and Cybernetics, 2009, p. 454-459.
Ekroth, R., et al., "Transcranial Doppler-estimated versus thermodilution estimated cerebral blood flow during cardiac operations. Influence of temperature and arterial carbon dioxide tension." Journal Thoracic Cardiovascular Surgery, 1991, 102(1): p. 95-102.
Gomez, C., et al., Transcranial Doppler Ultrasonographic Assessment of Intermittent Light Stimulation at Different Frequencies, Stroke, 1990, 21, p. 1746-1748.
Harrison, M. & Markus, H., "Estimation of cerebrovascular reactivity using transcranial Doppler, including the use of breath-holding as the vasodilatory stimulus", Stroke, 1992, 23(5) p. 668-73.
International Preliminary Report on Patentability dated Jul. 19, 2018, from application No. PCT/US2017/012395.
International Preliminary Report on Patentability dated Jul. 19, 2018, from application No. PCT/US2017/012365.
International Preliminary Report on Patentability dated Jul. 19, 2018, from application No. PCT/US2017/012402.
International Preliminary Report on Patentability dated Jul. 19, 2018, from application No. PCT/IB2017/050349.
International Preliminary Report on Patentability dated Nov. 8, 2018, from application No. PCT/US2017/029483.
Jaffres, P., et al., "Transcranial Doppler to detection admission patients at risk for neurological deterioration following mild and moderate brain trauma", Intensive Care Med, 2005, 31 (6): p. 785-790.
Japanese Office Action dated Aug. 28, 2018, from application No. 2016-554529.
Len, T.K., et al., "Cerebrovascular reactivity impairment after sport-induced concussion", Med Sci Sports Exerc, 2011, 43(12): p. 2241-2248.
Non-Final Office Action dated Sep. 17, 2018, from U.S. Appl. No. 15/156,175.
Uguz, H., "A hybrid system based on information gain and principal component analysis for the classification of transcranial Doppler signals", Computer Methods and Programs in Biomedicine, 2010, 107(2012) p. 598-609.
Zhu, X., "Semi-supervised Learning Literature Survey", Computer Sciences TR 1530, University of Wisconsin-Madison, 2008.
International Search Report and Written Opinion dated Jun. 1, 2017, from application No. PCT/IB2017/050349.
International Search Report and Written Opinion dated Jun. 8, 2017, from application No. PCT/US2017/012402.
Tatasurya, Samuel Radiant, "Multimodal Graphical User Interface for Ultrasound Machine Control via da Vinci Surgeon Console: Design, Development, and Initial Evaluation," The University of British Columbia, Vancouver, Aug. 2015, p. 33, paragraph 1.
International Preliminary Report on Patentability dated Dec. 28, 2017, from international application No. PCT/US2016/038433.
Chatelain et al. "Confidence-Driven Control of an Ultrasound Probe: Target-Specific Acoustic Window Optimization." IEEE ICRA May 16-21, 2016, pp. 3441-3446.
Chatelain et al. "Optimization of ultrasound image quality via visual servoing." IEEE INCRA May 26-30, 2015, pp. 5997-6002.

(56) References Cited

OTHER PUBLICATIONS

Mckinnon et al. "Long-Term Ambulatory Monitoring for Cerebral Emboli Using Transcranial Doppler Ultrasound." Stroke(35), 2004; pags 73-78.
Nadeau et al. "Intensity-Based Ultrasound Visual Servoing: Modeling and Validation with 2-D and 3-D Probes." IEEE Trans on Robotics (29:4), Aug. 2013, pp. 1003-1015.
Non-Final Office Action dated Jun. 27, 2018, from U.S. Appl. No. 15/942,368.
Qiu et al, "A Robotic Holder of Transcranial Doppler Probe for CBFV Auto-Searching." Proc of IEEE ICIA, Aug. 2013, pp. 1284-1289.
Souza-Daw et al. "Towards Ultrasonic Detection of Acoustic Windows for Transcranial Doppler Ultrasound and related Procedures." IEEE Proc INDS'11 & ISTET'11. Jul. 25-27, 2011. 6 pages.
Aggarwal, et al., "Noninvasive Monitoring of Cerebral Perfusion Pressure in Patients with Acute Liver Failure Using Transcranial Doppler Ultrasonography", Liver Transplantation, vol. 14, 2008, pp. 1048-1057.
Non-Final Office Action dated Jul. 8, 2019, from U.S. Appl. No. 15/156,175.
Almeida, V., et al., "Machine Learning Techniques for Arterial Pressure Waveform Analysis". Journal of Personalized Medicine, 2013. vol. 2, p. 82-101 (Year: 2013).
Baykal, N., et al., "Feature Discovery and Classification of Doppler Umbilical Artery Blood Flow Velocity Waveforms". Comput. Biol. Med., 1996. vol. 26. p. 451-462 (Year: 1996).
Extended European Search Report dated Jan. 4, 2019, from application No. 16812644.9.
Final Office Action dated Feb. 21, 2019, from U.S. Appl. No. 15/156,175.
Final Office Action dated Jan. 28, 2019, from U.S. Appl. No. 15/942,368.
Seker, H., et al., "Compensatory Fuzzy Neural Networks-Based Intelligent Detection of Abnormal Neonatal Cerebral Doppler Ultrasound Waveforms". IEEE Transactions on Information Technology in Biomedicine, 2001. vol. 5. p. 187-194 (Year: 2001).
Japanese Decision of Rejection dated Dec. 18, 2018, from application No. 2016-554529.
Non-Final Office Action dated Apr. 2, 2019, from U.S. Appl. No. 15/399,440.
Non-Final Office Action dated Mar. 19, 2019, from U.S. Appl. No. 15/399,648.
Final Office Action dated Jan. 30, 2020, from U.S. Appl. No. 15/497,039.
Japanese Office Action dated Jan. 27, 2020, from application No. 2018-534127.
Notice of Allowance dated Mar. 4, 2020, from U.S. Appl. No. 15/942,368.
Chinese Office Action dated Aug. 27, 2020, from application No. 201780005528.X.
Chinese Office Action dated Sep. 23, 2020, from application No. 201780005865.9.
Japanese Office Action dated Dec. 10, 2020, from application No. 2018-534916.
Japanese Office Action dated Mar. 11, 2021, from application No. 2018-555541.
Japanese Office Action dated Nov. 5, 2020, from application No. 2018-534904.
Japanese Office Action dated Oct. 22, 2020, from application No. 2018-534131.
Notice of Allowance dated Mar. 19, 2021, from U.S. Appl. No. 15/399,710.
European Office Action dated Sep. 24, 2021, from application No. 17735919.7.
European Office Action dated Sep. 28, 2021, from application No. 17736375.1.

\* cited by examiner

TRANSCRANIAL DOPPLER PROBE

CROSS-REFERENCE TO RELATED PATENT APPLICATIONS

The present disclosure claims priority to, and the benefit of, U.S. provisional patent application Ser. No. 62/181,859, titled AUTOMATIC DISCOVERY OF TRANSCRANIAL DOPPLER WINDOW, and filed on Jun. 19, 2015, which is incorporated herein by reference in its entirety. The present disclosure claims priority to, and the benefit of, U.S. provisional patent application Ser. No. 62/181,862, titled INITIAL PLACEMENT OF TRANSCRANIAL DOPPLER SENSORS, and filed on Jun. 19, 2015, which is incorporated herein by reference in its entirety. The present disclosure claims priority to, and the benefit of, U.S. provisional patent application Ser. No. 62/347,527, titled PROBE SUPPORT STRUCTURE WITH VARIABLE STIFFNESS, and filed on Jun. 8, 2016, which is incorporated herein by reference in its entirety.

FIELD

Subject matter described herein relates generally to medical devices, and more particularly to a headset including a probe for diagnosing medical conditions.

BACKGROUND

Transcranial Doppler (TCD) is used to measure the cerebral blood flow velocity (CBFV) in the major conducting arteries of the brain (e.g., the Circle of Willis) non-invasively. It is used in the diagnosis and monitoring a number of neurologic conditions, such the assessment of arteries after a subarachnoid hemorrhage (SAH), aiding preventative care in children with sickle cell anemia, and risk assessment in embolic stroke patients.

Traditionally, a TCD ultrasound includes the manual positioning of a probe relative to a patient by a technician. The probe emits energy into the head of a patient. The technician identifies the CBFV waveform signature of a cerebral artery or vein in the head. Identification of the signal requires integration of probe insonation depth, angle, and placement within one of several ultrasound windows as well as characteristics from the ultrasound signal which include waveform spectrum, sounds, M-Mode, and velocity. For devices utilizing a probe (e.g., an automated Transcranial Doppler device), there exist concerns related to alignment and pressure that the probe exerts during use (e.g., for comfortability and safety when held against a human being or for ensuring the effectiveness of the probe). In some devices, a spring is incorporated within a probe, but such devices may not be effective for pressure control due to lateral slippage and shifting of the spring within the probe.

SUMMARY

According to various embodiments, there is provided a headset mountable on a head, the headset including a probe for emitting energy into the head. The headset may further include a support structure coupled to the probe, with the support structure including translation actuators for translating the probe along at least two axes generally parallel to a surface of the head.

In some embodiments, the headset may further include at least a perpendicular translation actuator for translating the probe along a perpendicular axis generally perpendicular to the surface of the head. In some embodiments, the headset may further include at least one rotation actuator for rotating the probe about at least one rotation axis. The headset may further include a tilt axis generally orthogonal to the perpendicular axis. The headset may further include a pan axis generally orthogonal to the perpendicular axis.

In some embodiments, the headset may provide exactly five degrees of freedom of movement of the probe including translation through the two axes generally parallel to the surface of the head, one degree of freedom through the perpendicular axis generally perpendicular to the surface of the head, one degree of freedom along the tilt axis, and one degree of freedom along the pan axis.

According to various embodiments, there is provided a device configured to interact with a target surface, the device including a probe configured to interact with the target surface. The device may further include a support structure coupled to the probe for moving the probe relative to the target surface. The support structure may be configured to translate the probe along both a translation plane generally parallel to the target surface. The support structure may be further configured to rotate the probe about at least one rotation axis.

In some embodiments, the support structure is configured to translate the probe along a translation axis generally perpendicular to the translation plane. In some embodiments, the support structure includes a tilt axis different than the translation axis. In some embodiments, the support structure includes a pan axis different than the translation axis and the tilt axis. In some embodiments, the support structure is further configured to rotate the probe towards and away from the target surface about the tilt axis and the pan axis. In some embodiments, the support structure has a stiffness along each of the translation plane and the translation axis, and the stiffness along the translation plane is greater than the stiffness along the translation axis. In some embodiments, the probe is configured to emit ultrasound waves into the target surface.

In some embodiments, the device further includes a first actuator configured to translate the probe along a first direction along the translation plane. In some embodiments, the device further includes a second actuator configured to translate the probe along a second direction perpendicular to the first direction along the translation plane. In some embodiments, the device further includes a third actuator configured to translate the probe along the translation axis. In some embodiments, the first actuator and the second actuator are configured with a stiffness of the translation plane, and the third actuator is configured with a stiffness of the translation axis. In some embodiments, the first, second, and third actuators are a servo motor.

In some embodiments, an input force of each of the first, second, and third actuators is determined by a method including determining a configuration of the support structure for the probe and each of the first, second, and third actuators for the support structure. In some embodiments, the method further includes determining a stiffness matrix for the support structure based on the configuration of the support structure and a desired conditional stiffness of the support structure. In some embodiments, the method further includes determining a force vector by multiplying the stiffness matrix and a vector of a difference of the desired and actual translational and rotational position of the probe. In some embodiments, the method further includes calculating a Jacobian for the support structure. In some embodiments, the method further includes determining the input forces for each of the first, second, and third actuators by multiplying the force vector and a transpose of the Jacobian.

According to various embodiments, there is provided a method of manufacturing a device configured to interact with a target surface, including providing a probe configured to interact with the target surface. In some embodiments, the method further includes coupling a support structure to the probe for moving the probe relative to the target surface, wherein the support structure configured to translate the probe along both a translation plane generally parallel to the target surface and along a translation axis generally perpendicular to the translation plane and rotate the probe about at least one rotation axis. In some embodiments, the one rotation axis includes a tilt axis different than the translation axis. In some embodiments the one rotation axis includes a pan axis different than the translation axis and the tilt axis.

BRIEF DESCRIPTION OF THE DRAWINGS

Features, aspects, and advantages of the present invention will become apparent from the following description and the accompanying exemplary embodiments shown in the drawings, which are briefly described below.

DETAILED DESCRIPTION

Figure 1:
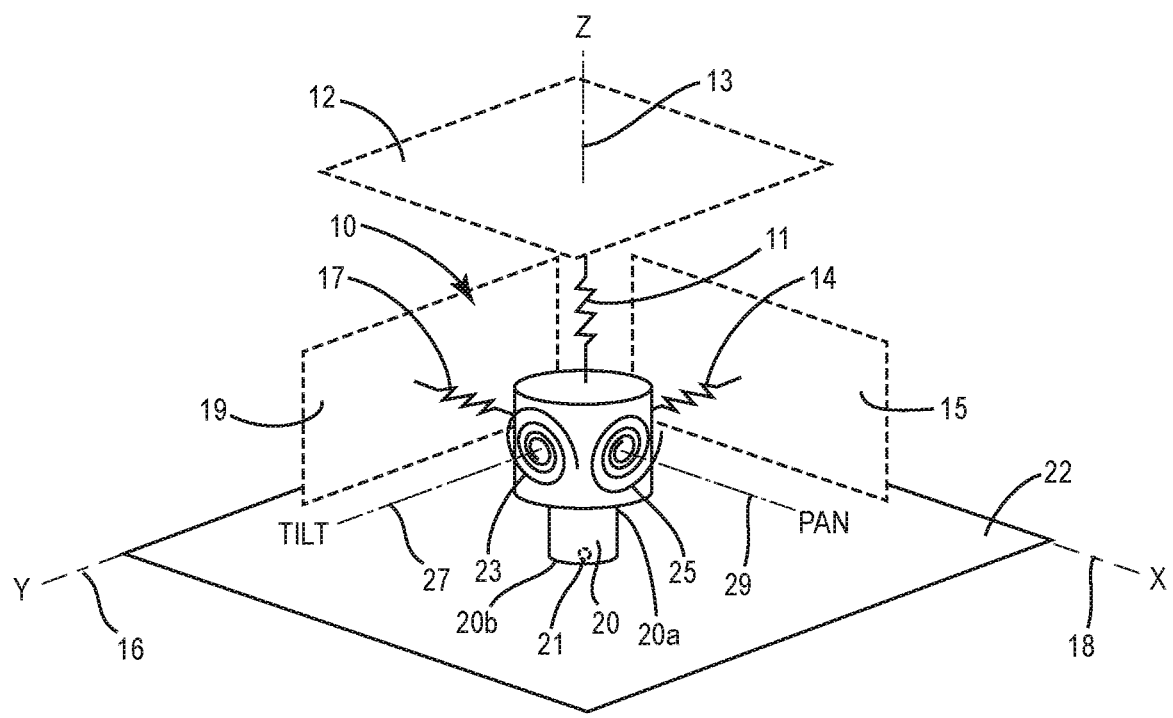
FIG. 1 is a diagram of a virtual support structure for manipulating a medical probe, according to an exemplary embodiment.

The detailed description set forth below in connection with the appended drawings is intended as a description of various configurations and is not intended to represent the only configurations in which the concepts described herein may be practiced. The detailed description includes specific details for providing a thorough understanding of various concepts. However, it will be apparent to those skilled in the art that these concepts may be practiced without these specific details. In some instances, well-known structures and components are shown in block diagram form in order to avoid obscuring such concepts.

According to various embodiments, a five degree of freedom (DOF) kinematic mechanism is used that fully automates evaluation of the temporal window quality and can rediscover the temporal window even after complete loss of signal. In some embodiments, a computer generates and directs the mechanism to translate and reorient the probe along the surface of the head until a candidate signal is located. Once located, the probe is reoriented to increase signal strength. In some embodiments, reducing the search time of the automated system to discover the temporal window is accomplished by aligning the mechanism and probe at a known anatomical feature. In some embodiments, the alignment is performed with a visual window guide for the user to place the probe at an initial starting point along the zygomatic arch between ear and the eye.

In some embodiments, after the probe is properly aligned, the compliance of the probe is held normal to the surface at a high enough level to keep the probe seated, but low enough so to be comfortable to the user, as the probe moves in and out following the surface of the head. In some embodiments, the X and Y axes can retain a higher servo stiffness in order to maintain precision control of probe location. In some embodiments, since the normal force of the probe is determined by the Z-axis stiffness, the sliding force encounter by the X and Y axes will be limited to a comfortable level, and the probe can be directed to perform a search for the TCD window. In some embodiments, if the orientation of the probe needs to be changed, the orientation stiffnesses can be increased via software.

In some embodiments, the kinematic mechanism of the probe includes five motor degrees of freedom, Q={J1, J2, J3, J4, J5} (i.e., motor or joint space) to effect five degrees of freedom in position and orientation X={x, y, z, pan, tilt} (i.e., task space). As such, the forward kinematics may be written as the relationship between motor coordinates and probe coordinates: X=fwd_kin(Q), where fwd_kin is a function representing a series of equations based on the mechanism design and typically analyzed by Denavit-Hartenberg parameters.

In some embodiments, placement of the TCD probe is specified via the inverse kinematics with either an analytic inverse solution: Q=inv_kin(X), or by using a numerical differential such as the Jacobian inverse solution $dQ_{cmd}(n) = J^{-1}(X_{err}(n))$, where J is the Jacobian, relating differential motion of the motors to the differential motion of the probe, $X_{err}(n)$ is the probe position and orientation error at time n, and $dQ_{cmd}(n)$ is the differential motor command at time n.

FIG. 1 is a diagram of a model of a virtual support structure 10 for a probe 20, according to an exemplary embodiment. The support structure 10 is configured to position the probe 20 relative to a target surface 22. In some embodiments, the probe 20 is a medical probe, such as a medical probe for use with a transcranial Doppler (TCD) apparatus to emit ultrasound wave emissions directed to the target surface 22. In other embodiments, the probe 20 is configured to emit other types of waves during operation, such as, but not limited to, infrared waves, x-rays, and so on.

In some embodiments, the probe 20 has a first end 20a and a second end 20b. In some embodiments, the first end 20a interfaces with the support structure 10. In some embodiments, the second end 20b contacts the target surface 22 on which the probe 20 operates at a contact point 21. In some embodiments, the second end 20b is a concave structure such that the contact point 21 is a ring shape (i.e., the second end 20b contacts the target surface 22 along a circular outer edge of the concave second end 20b). The support structure 10 controls the relative position of the probe 20 (e.g., z-axis pressure, y-axis pressure, x-axis pressure, normal alignment, etc.). The support structure 10 is shown as a virtual structure including a first virtual spring 11 coupled between the probe 20 and a virtual surface 12 and exerting a force along a z-axis 13, a second virtual spring 14 coupled between the probe 20 and a virtual surface 15 and exerting a force along a y-axis 16, and a third virtual spring 17 coupled between the probe 20 and a virtual surface 19 and exerting a force along the x-axis 18. The virtual support structure 10 further includes a torsional spring 23 exerting a torque about a tilt axis 27 and a second torsional spring 25 exerting a torque about a pan axis 29. In some embodiments, the virtual support structure 10 includes other virtual elements, such as virtual dampers (not shown). Virtual dampers represent elements that improve the stability of the system and are useful for tuning the dynamic response of the system.

The virtual support structure 10 represents a variety of mechanical structures that may be utilized to position the probe 20 relative to the target surface 22, as described in more detail below. In some embodiments, the second end 20b of the probe 20 is caused to contact a relatively delicate surface, such as the skin of the patient. The support structure is configured to adjust its stiffness (e.g., impedance, compliance, etc.) to provide variable linear forces and rotational forces on the probe 20, and may be relatively stiff in some directions and may be relatively compliant in other directions. For example, the support structure 10 may apply minimal force and may be relatively compliant along the z-axis 13 to minimize forces applied to the patient (e.g., if the patient moves relative to the support structure) in a direction generally normal to the target surface 22 and may be relatively stiff along the y-axis 16 and the x-axis 18 to improve the positional accuracy and precision of the probe 20 along a plane generally parallel to the target surface 22. Further, the desired stiffness of the support structure 10 along various axes may vary over time, depending on the task at hand. For example, the support structure may be configured to be relatively compliant in scenarios in which the support structure 10 is being moved relative to the patient (e.g., during initial set-up of the probe structure, removal of the probe structure, etc.), or when it is advantageous to be relatively free-moving (e.g., during maintenance/cleaning, etc.), and may be configured to be relatively stiff, in some directions, in scenarios in which accuracy and precision of the positioning of the probe 20 is advantageous (e.g., during the TCD procedure or other procedure being performed with the probe 20).

As described in more detail below, a kinematic model of the support structure 10 can be utilized to calculate the relationship between the forces applied to the target surface 22 by the probe 20 and the forces (e.g., torques) applied by actuators actuating the support structure 10. The forces applied to the target surface 22 by the probe 20 in the idealized system can therefore be determined theoretically, without direct force sensing, thereby eliminating the need for a load cell disposed in-line with the probe 20 and/or a torque sensor coupled to the probe 20. In a physical system, static friction, along with other unmodeled physical effects, may introduce some uncertainty.

Figure 2:
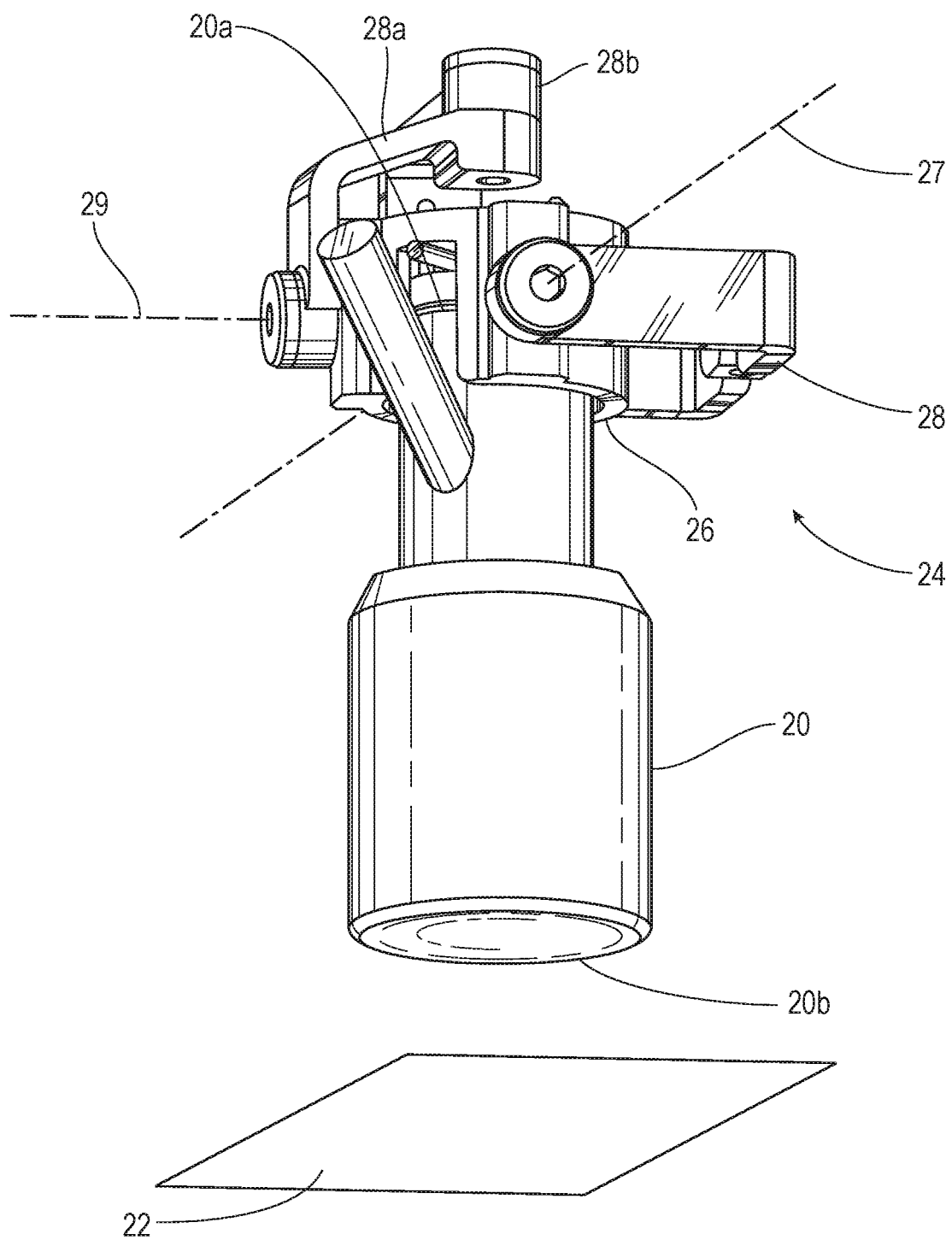
FIG. 2 is an perspective view of a medical probe and a gimbal structure, according to an exemplary embodiment.

Referring to FIG. 2, the probe 20 is shown according to an exemplary embodiment mounted to a portion of a support structure, shown as a gimbal structure 24, which can rotate about multiple axes, at the first end 20a. The gimbal structure 24 includes a first frame member 26 that is able to rotate about the tilt axis 27 and a second frame member 28 that is able to rotate about the pan axis 29. The target surface 22 may be uneven (e.g., non-planar). The gimbal structure 24 allows the probe 20 to be oriented such that it is normal to the target surface 22 at the contact point 21.

Figure 3:
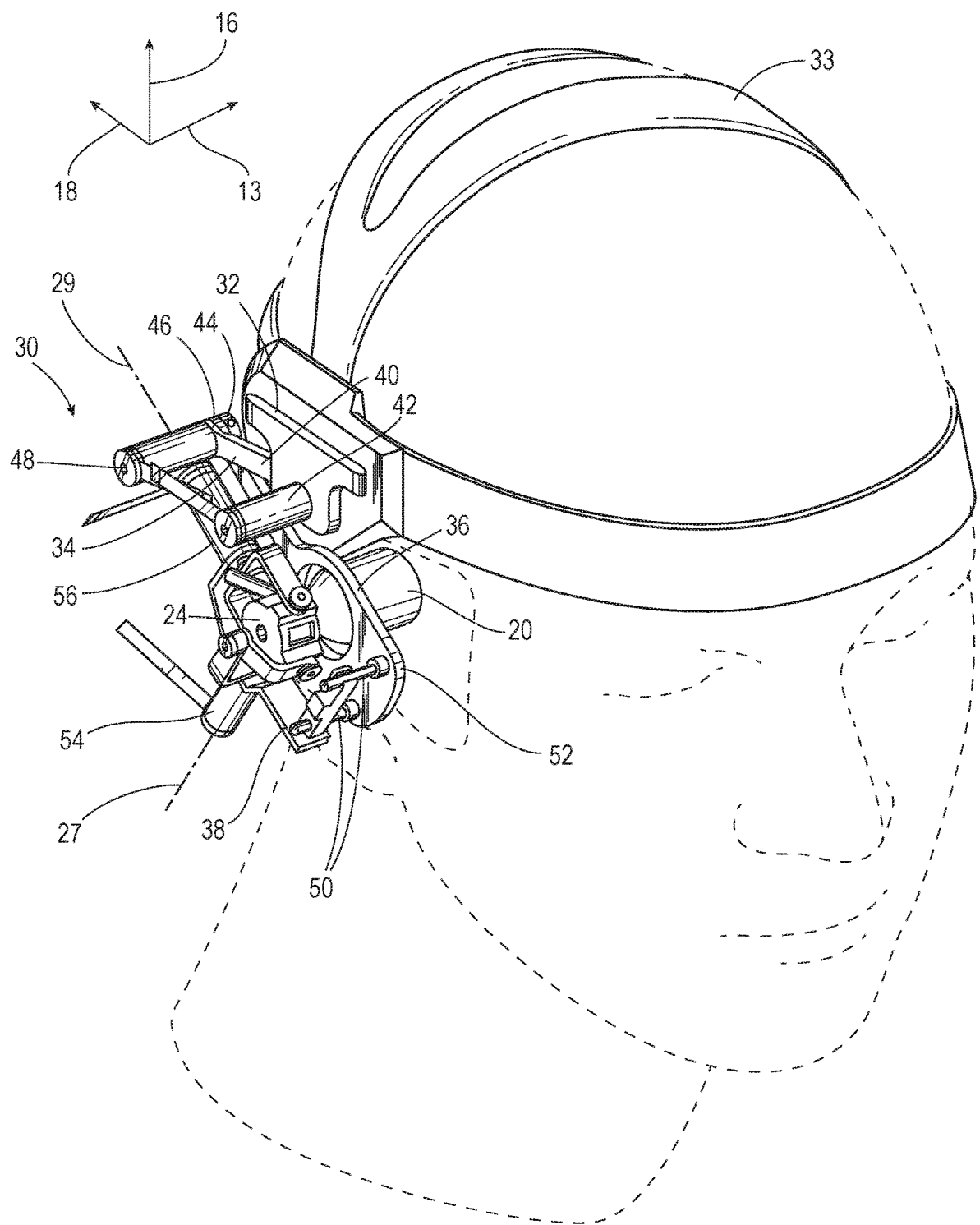
FIG. 3 is a perspective view of a two-link revolute support structure for the medical probe of FIG. 2, according to an exemplary embodiment.
Figure 4:
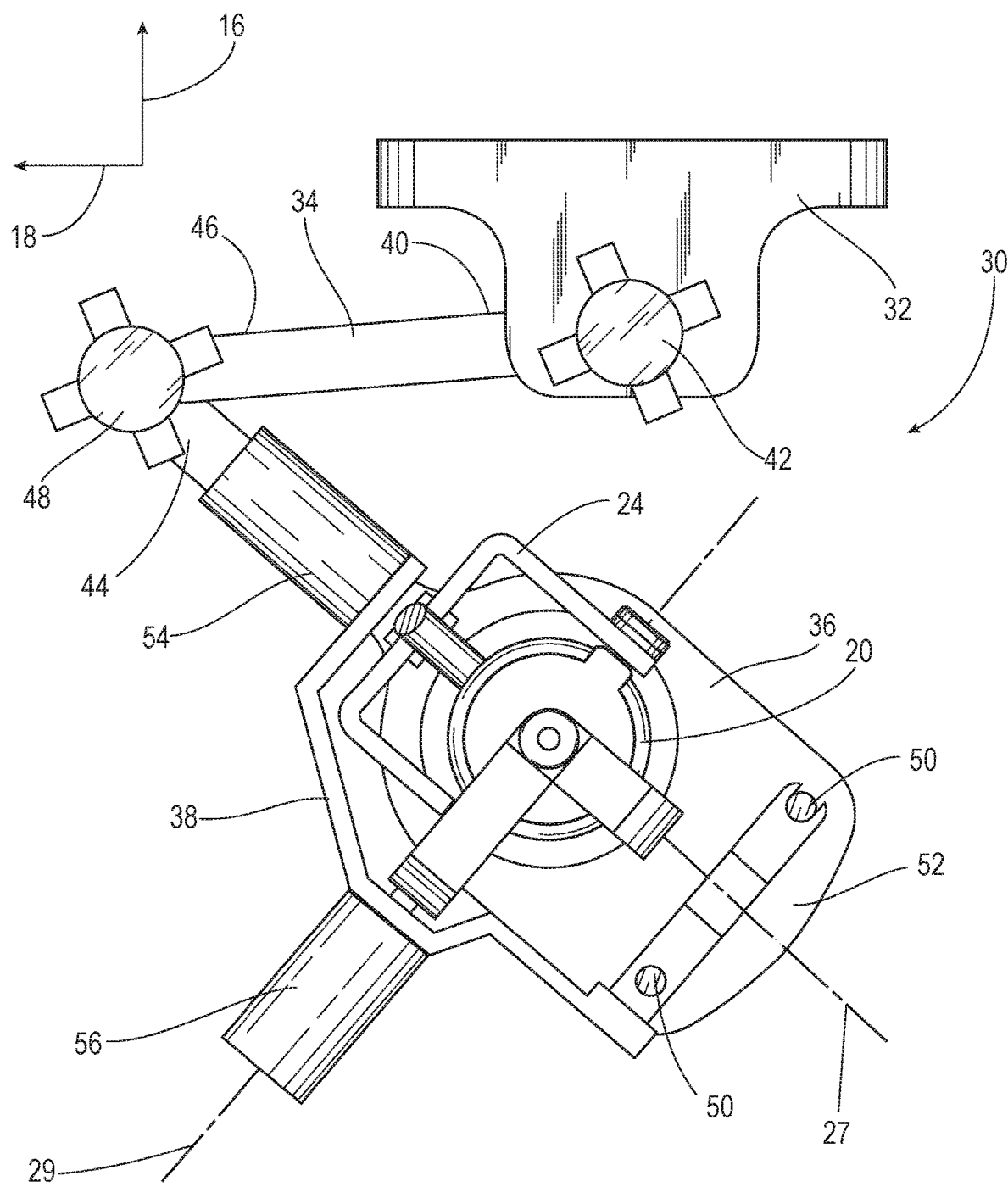
FIG. 4 is front elevation view of the support structure of FIG. 3.
Figure 5:
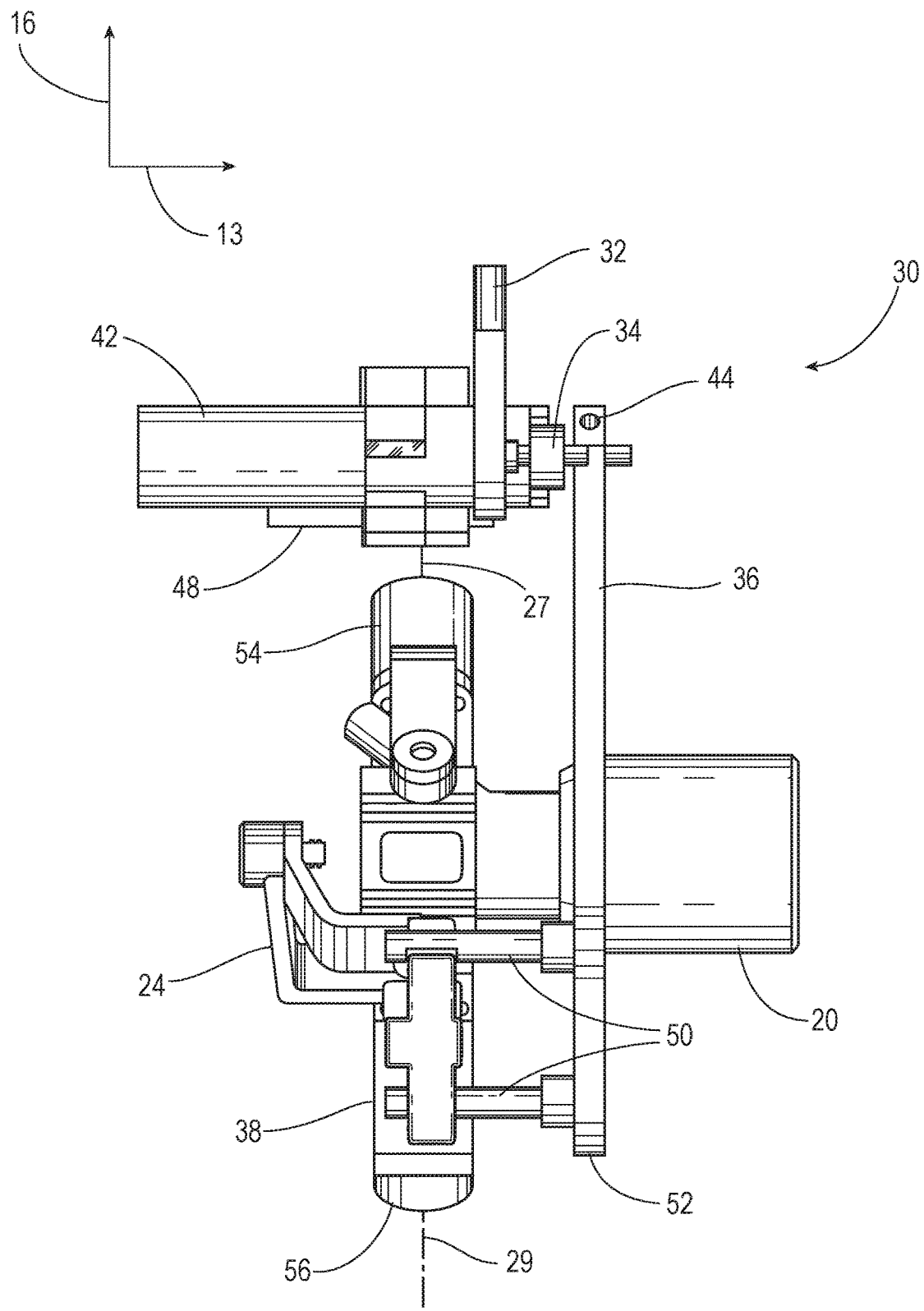
FIG. 5 is a right side elevation view of the support structure of FIG. 3.

Referring now to FIGS. 3-5, a support structure 30 for the probe 20 is shown according to an exemplary embodiment as a two-link revolute (e.g., revolute-revolute) robot. The support structure 30 includes a first frame member 32, a second frame member 34, a third frame member 36, a fourth frame member 38, and the gimbal structure 24. The first frame member 32 is configured to be a static member. The first frame member 32 may, for example, be mounted to a halo or headset 33 worn on the patient's head or other structure that attaches the first frame member 32 to the patient or fixes the position of the first frame member 32 relative to the patient. The probe 20 is configured to emit energy into the head of the patient.

The second frame member 34 is a link configured to rotate about the z-axis 13. The z-axis 13 is generally perpendicular to the surface of the head. A first end 40 of the second frame member 34 is coupled to the first frame member 32. According to an exemplary embodiment, the rotation of the second frame member 34 relative to the first frame member 32 is controlled by an actuator 42, shown as an electric motor and gearbox that is attached through the first frame member 32. Actuator 42 acts as a perpendicular translation actuator for translating the probe along a perpendicular axis generally perpendicular to the surface of the head.

The third frame member 36 is a link configured to rotate about the z-axis 13. A first end 44 of the third frame member 36 is coupled to a second end 46 of the second frame member 34. According to an exemplary embodiment, the rotation of the third frame member 36 relative to the second frame member 34 is controlled by an actuator 48, shown as an electric motor and gearbox that is attached through the second frame member 34.

The fourth frame member 38 is configured to translate along the z-axis 13 (e.g., in and out, in and away from the head, etc.). According to an exemplary embodiment, the fourth frame member 38 slides along rail members 50 that are fixed to a second end 52 of the third frame member 36. The position of the fourth frame member 38 relative to the third frame member 36 is controlled by an actuator, such as an electric motor and a lead screw (not shown for clarity).

The gimbal structure 24 and the probe 20 are mounted to the fourth frame member 38. The gimbal structure 24 controls the orientation of the probe 20 about the tilt axis 27 and the pan axis 29 (e.g., pan and tilt). The position of the probe 20 about the tilt axis 27 is controlled by an actuator 54, shown as an electric motor and gearbox. Actuator 54 acts as a rotation actuator to rotate the probe. The position of the probe 20 about the pan axis 29 is controlled by an actuator 56, shown as an electric motor and gearbox. Actuator 56 acts as a rotation actuator to rotate the probe. In one embodiment, the rotation of the probe 20 about the tilt axis 27 and the pan axis 29 is different than the z-axis 13, regardless of the rotation of the frame members 34 and 36.

The probe 20 is able to move on the x-y plane, i.e., the translation plane, which is defined by the x-axis 18 and the y-axis 16, through the rotation of the second frame member 34 and the third frame member 36. The probe 20 is able to move along the z-axis 13, i.e., the translation axis, through the translation of the fourth frame member 38. Further, the probe 20 is able to rotate about tilt axis 27 and the pan axis 29 through the gimbal structure 24. Combining these five degrees of freedom allows the position and orientation of the probe 20 relative to the target surface 22 to be completely described and controlled, discounting rotation about a third axis that is orthogonal to the pan axis 29 and the tilt axis 27.

According to an exemplary embodiment, the actuators utilized to position the support structure 30 are servo motors. The use of servo motors to control the support structure allow for a more precise control, compared to a stepper motor, for the torque output, rotational position, and angular speed of the motor, as well as the corresponding position of the probe 20 and the interaction between the probe 20 and the target surface 22. Of course, other suitable motors known to those of ordinary skill in the art could also be used.

Figure 6:
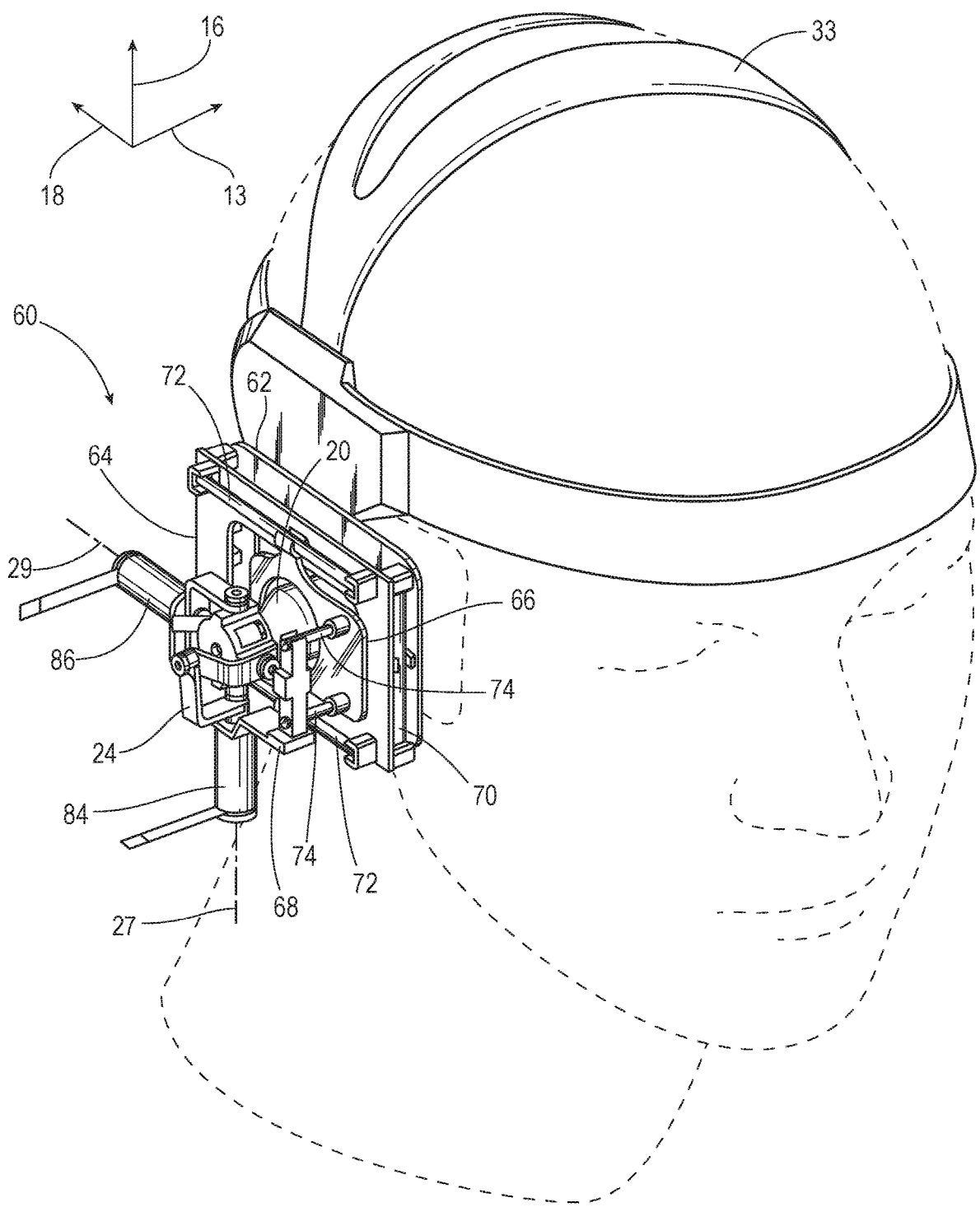
FIG. 6 is a perspective view of a prismatic support structure for the medical probe of FIG. 2, according to an exemplary embodiment.
Figure 7:
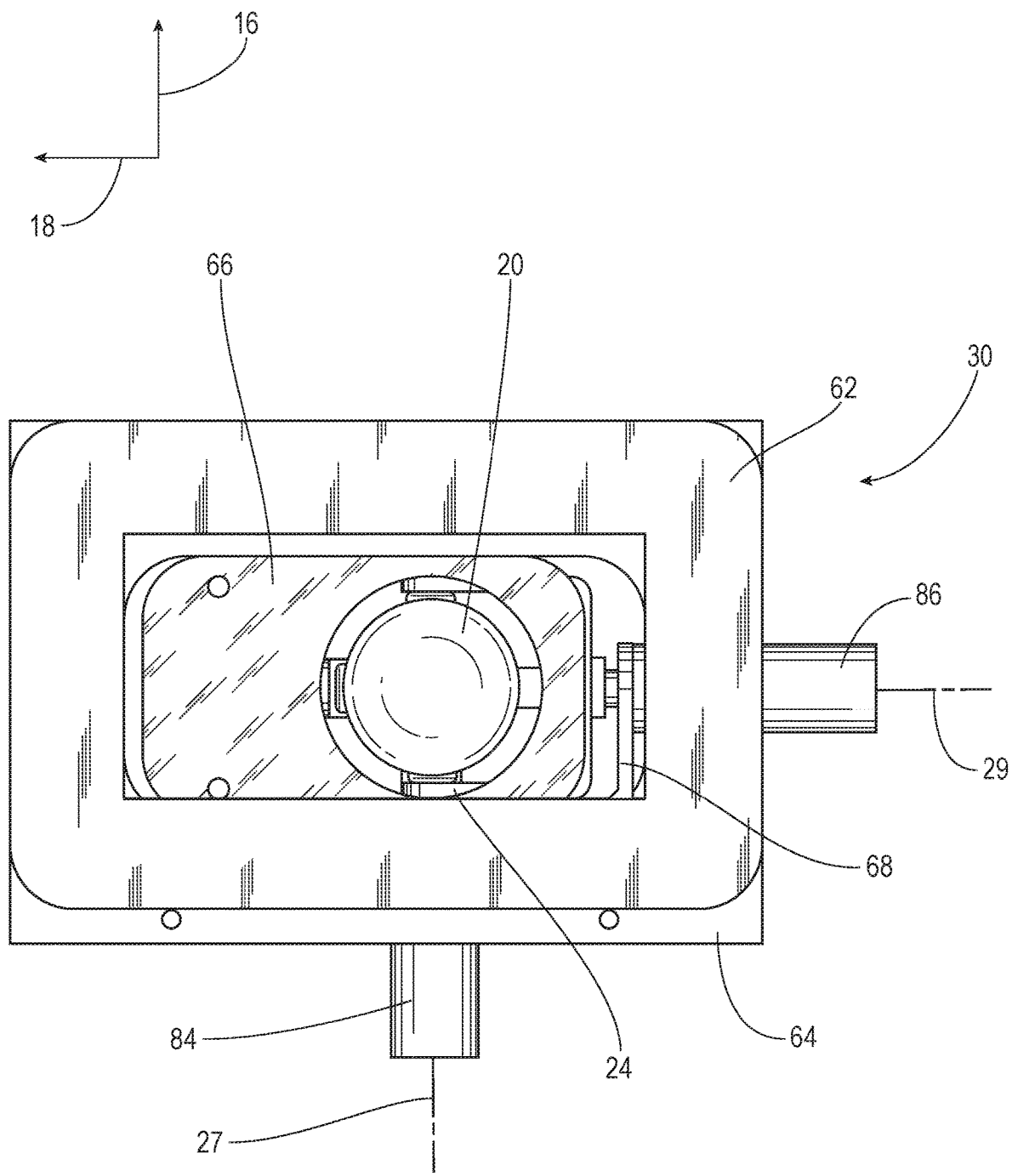
FIG. 7 is front elevation view of the support structure of FIG. 6.
Figure 8:
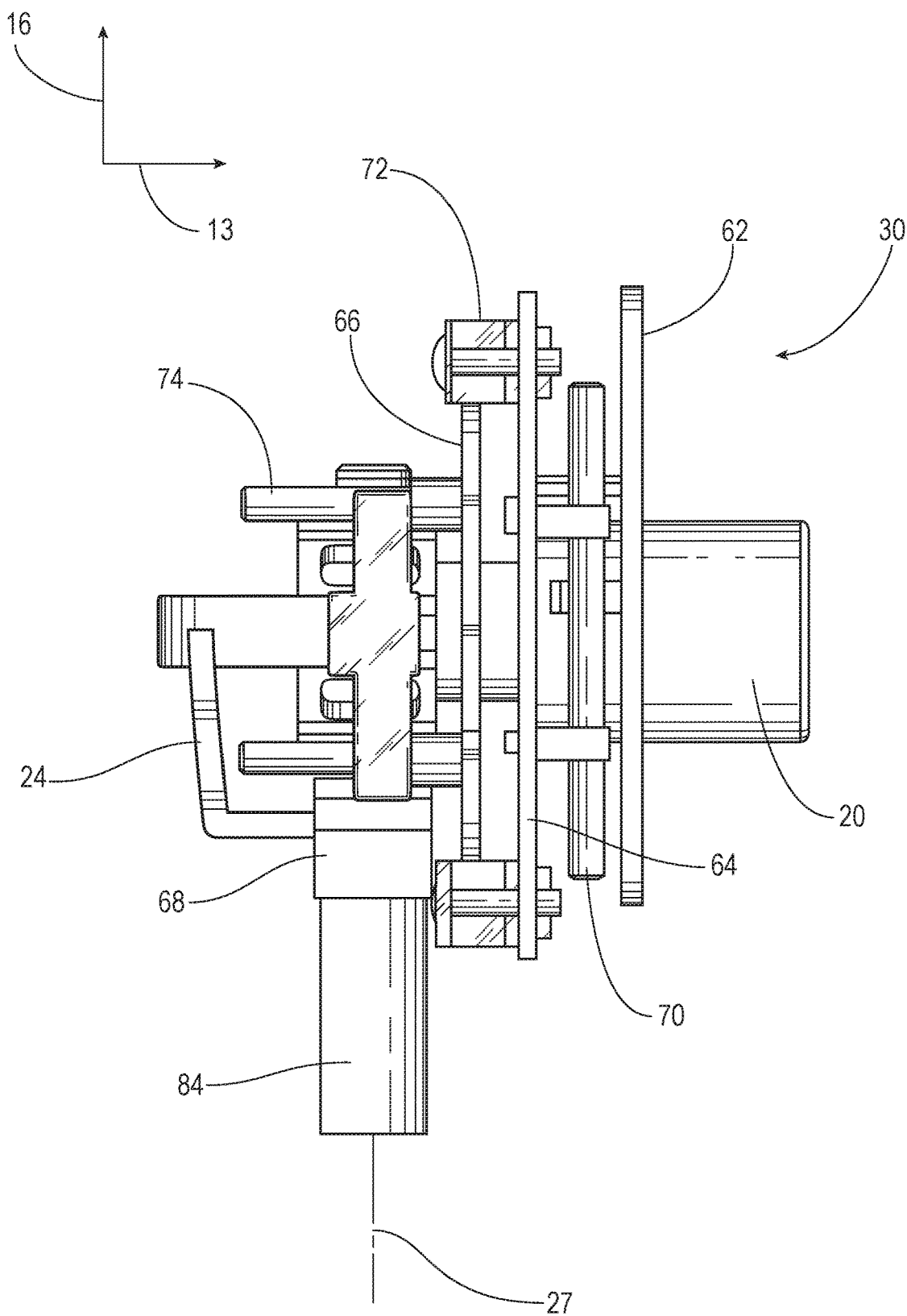
FIG. 8 is a right side elevation view of the support structure of FIG. 6.

Referring now to FIGS. 6-8, a support structure 60 for the probe 20 and the gimbal structure 24 is shown according to another exemplary embodiment as a prismatic (e.g., Cartesian, rectilinear, etc.) robot. The support structure 60 includes a first frame member 62, a second frame member 64, a third frame member 66, a fourth frame member 68, and the gimbal structure 24. The first frame member 62 is configured to be a static member. The first frame member 62 may, for example, be mounted to a halo or headset 33 worn on the patient's head or other structure that fixes the position of the first frame member 62 relative to the patient.

The second frame member 64 is configured to translate along the y-axis 16 (e.g., up and down, bottom of ear to top of ear, etc). According to an exemplary embodiment, the second frame member 64 slides along rail members 70 that are fixed to the first frame member 62. The position of the second frame member 64 relative to the first frame member 62 is controlled by an actuator, such as an electric motor and a lead screw (not shown for clarity).

The third frame member 66 is configured to translate along the x-axis 18 (e.g., forward and backward, ear to eye, etc.). According to an exemplary embodiment, the third frame member 66 slides along rail members 72 that are fixed to the second frame member 64. The rail members 72 are orthogonal to the rail members 70. The position of the third frame member 66 relative to the second frame member 64 is controlled by an actuator, such as an electric motor and a lead screw (not shown for clarity).

The fourth frame member 68 is configured to translate along the z-axis 13 (e.g., in and out, in and away from the head, etc.). According to an exemplary embodiment, the fourth frame member 68 slides along rail members 74 that are fixed to the third frame member 66. The position of the fourth frame member 68 relative to the third frame member 66 is controlled by an actuator, such as an electric motor and a lead screw (not shown for clarity).

The gimbal structure 24 and the probe 20 are mounted to the fourth frame member 68. The gimbal structure 24 controls the orientation of the probe 20 about the tilt axis 27 and the pan axis 29 (e.g., tilt and pan). The position of the probe 20 about the tilt axis 27 is controlled by an actuator 84, shown as an electric motor and gearbox. The position of the probe 20 about the pan axis 29 is controlled by an actuator 86, shown as an electric motor and gearbox.

The probe 20 is able to move on the x-y plane through the translation of the second frame member 64 and the third frame member 66, move along the z-axis 13 through the translation of the fourth frame member 68, and rotate about tilt axis 27 and the pan axis 29 through the gimbal structure 24. Combining these five degrees of freedom allows the position and orientation of the probe 20 relative to the target surface 22 to be completely described and controlled, discounting rotation about a third axis that is orthogonal to the pan axis 29 and the tilt axis 27.

A kinematic model can be developed for any embodiment of a support structure for the probe 20 to determine the relationship between the forces exerted at the probe 20 and the forces applied by the actuators controlling the support structure.

A stiffness matrix for the support structure is first determined. The stiffness matrix is determined using a multitude of variables, including the physical properties of the support structure (e.g., the geometry of the frame members, the stiffness of the individual frame members etc.), the system stiffness along the chosen coordinate system axis, and a velocity-based term for system damping. According to an exemplary embodiment, the desired stiffness of the support structure is defined in the z direction ($K_z$), the y direction ($K_y$), and the x direction ($K_x$)(e.g., as represented by the virtual springs 11, 14, and 17 in FIG. 1), and about the pan axis 29 ($K\omega_x$) and about the tilt axis 27 ($K\omega_y$)(e.g., as represented by the virtual torsional springs 23 and 25 in FIG. 1). As described above, in some embodiments, the virtual stiffnesses vary over time and are based on the task being accomplished with the probe 20. For example, stiffness in the y direction and in the x direction may have a lower bound corresponding to a relatively low lateral stiffness during a set-up or removal procedure, in which the support structure is configured to be relatively compliant; and an upper bound corresponding to a relatively high stiffness during a scanning procedure, in which the support structure is configured to be relatively stiff, allowing for a more accurate positioning of the probe 20. Likewise, stiffness in the z direction may have a lower bound corresponding to a relatively low stiffness during initial positioning of the probe 20 in the z direction, in which the support structure is configured to be relatively compliant to allow the probe 20 to self-align (e.g., to minimize discomfort for the patient); and an upper bound corresponding to a relatively high stiffness during a scanning procedure, in which the support structure is configured to more stiff, to overcome friction forces between the probe 20 and the target surface 22 and to maintain the orientation of the probe 20. Further, rotational stiffnesses about the y axis and the x axis may have a lower bound corresponding to a relatively low rotational stiffness during positioning of the probe 20 to conform to the contour of the target surface 22 (e.g., the head of the patient), in which the support structure (e.g., the gimbal structure 24) is configured to be relatively compliant (e.g., to minimize discomfort for the patient); and an upper bound corresponding to a relatively high rotational stiffness when a more accurate positioning (e.g., panning, tilting, etc.) of the probe 20 is desired.

A force vector is then derived using the following equation:

$$\vec{F} = K\Delta\vec{x} \qquad \text{(Eq. 1)}$$

where K is the stiffness matrix and $\Delta\vec{x}$ is the vector of the difference of the desired and actual translational position in the x, y, and z directions and rotational position about the x-axis 18 and y-axis 16 of the probe 20.

The force applied by the actuators (e.g., the torque applied by rotational actuators) controlling the position of the support structure may then be determined using the following equation:

$$\tau = J^T \vec{F} \qquad \text{(Eq. 2)}$$

where $J^T$ is the Jacobian transpose determined by the kinematics of the specific support structure. The Jacobian is the differential relationship between the joint positions and the end-effector position and orientation (e.g., the position of the probe 20). The joint positions are either in units of radians (e.g., for rotational joints), or in units of length (e.g., for prismatic or linear joints). The Jacobian is not static and changes as the support structure position articulates.

Figure 9:
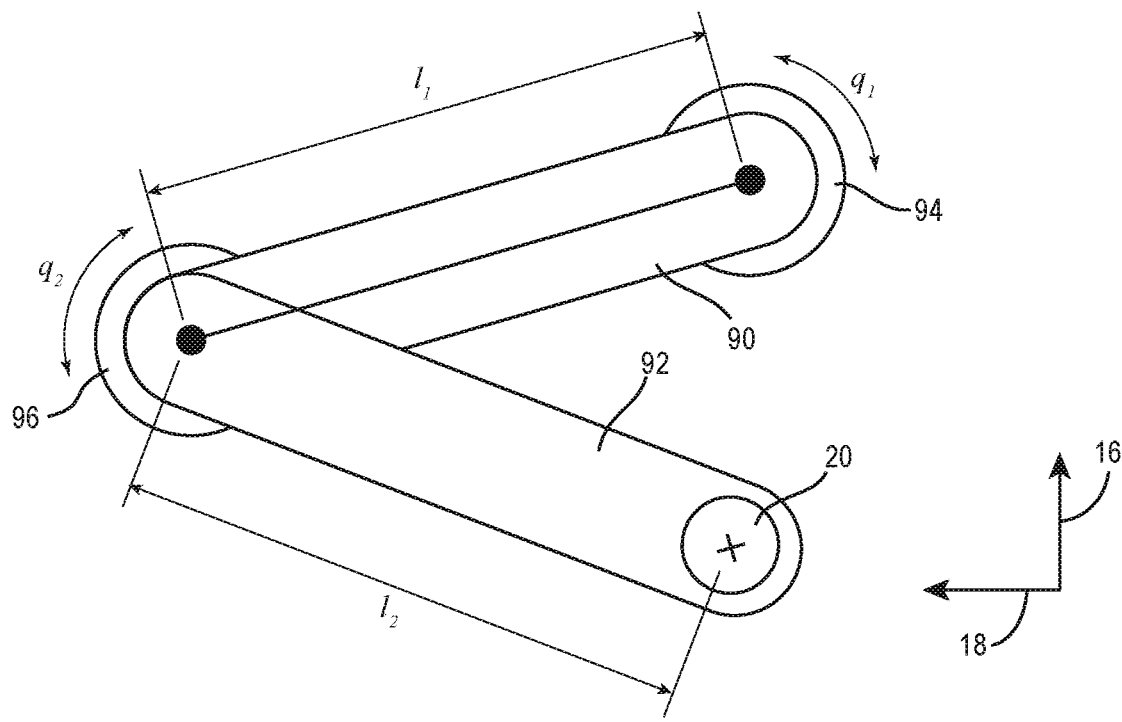
FIG. 9 is a schematic front view diagram of the support structure of FIG. 3.

Referring now to FIG. 9, a schematic front view diagram of the support structure 30 is shown. The second frame member 34 is represented by a first link 90, having a length $l_1$. The first link 90 is articulated by a rotary actuator 94, the rotation of which is shown as $q_1$. The third frame member 36 is represented by a second link 92, having a length $l_2$. The second link 92 is articulated by a rotary actuator 96, the rotation of which is shown as $q_2$. The actuators 94 and 96 move the probe 20 in the x-y plane.

The forward kinematics of this device are:

$c_1 = \cos(q_1), s_1 = \sin(q_1)$ $c_{12} = \cos(q_1+q_2), s_{12} = \sin(q_1+q_2)$ $x = l_1 c_1 + l_2 c_{12}$ (Eq. 3)

$y = l_1 s_1 + l_2 s_{12}$ (Eq. 4)

The Jacobian for such a revolute-revolute robot is derived by taking the partial derivative of the forward kinematics with respect to both $q_1$ and $q_2$.

$$J = \begin{bmatrix} -l_1 s_1 - l_2 s_{12} & -l_2 s_{12} \\ l_1 c_1 + l_2 c_{12} & l_2 c_{12} \end{bmatrix}$$ (Eq. 5)

The Jacobian shown in Equation 5 is the Jacobian for the Cartesian movement of the revolute-revolute robot on the x-y plane (e.g., translation along the y-axis 16 and the x-axis 18), describing the differential relationship between joint motion and probe motion. One of ordinary skill in the art would understand that in other embodiments, additional terms may be included in the Jacobian to describe the differential relationship between the motion of the probe 20 and other motions of the robot (e.g., rotation of the probe 20 about the tilt axis 27 and the pan axis 29 and translation along the z-axis 13).

Figure 10:
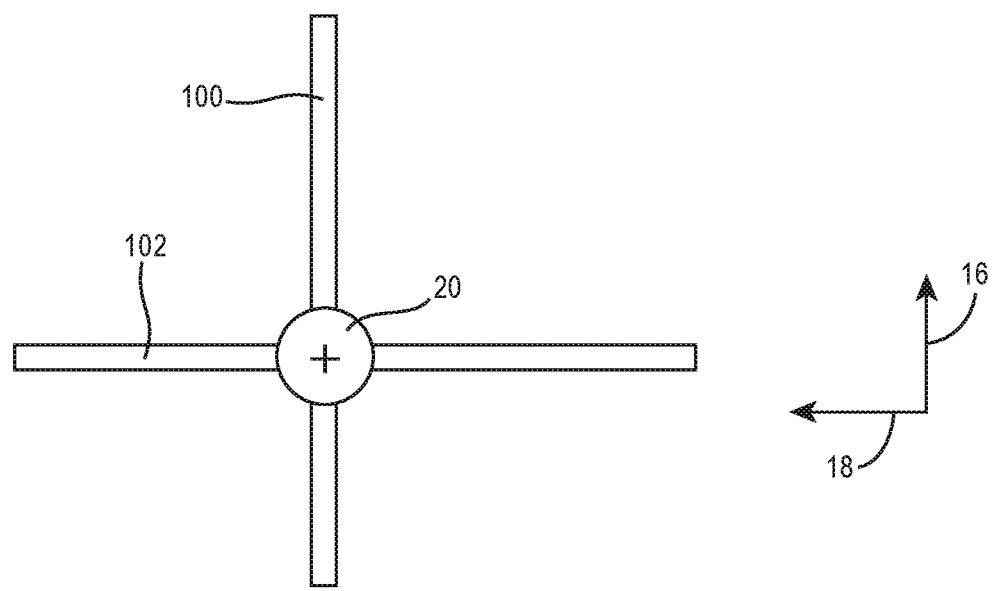
FIG. 10 is a schematic front view diagram of the support structure of FIG. 6.

Referring now to FIG. 10, a schematic front view diagram of the support structure 60 is shown. The probe 20 is moved in the y direction by a first linear actuator 100 (e.g., an electric motor and lead screw) and is moved in the x direction by a second linear actuator 102 (e.g., an electric motor and lead screw). The actuators 100 and 102 move the probe 20 in the x-y plane. Because each joint is orthogonal to the other, and has a one to one mapping of joint motion to Cartesian motion, the Jacobian for such a prismatic robot becomes the identity matrix:

$$J = \begin{bmatrix} 1 & 0 \\ 0 & 1 \end{bmatrix}$$ (Eq. 6)

The Jacobian shown in Equation 6 is the Jacobian for the Cartesian movement of the prismatic robot on the x-y plane (e.g., translation along the y-axis 16 and the x-axis 18), describing the differential relationship between joint motion and probe motion. In other embodiments, additional terms may be included in the Jacobian to describe the differential relationship between the motion of the probe 20 and other motions of the robot (e.g., rotation of the probe 20 about the tilt axis 27 and the pan axis 29 and translation along the z-axis 13).

The support structure 30 controls the position of the probe 20 in the z direction with the translation of the fourth frame member 38 with a single linear actuator (e.g., an electric motor and lead screw). Similarly, the support structure 60 controls the position of the probe 20 in the z direction with the translation of the fourth frame member 68 with a single linear actuator (e.g., an electric motor and lead screw). For either support structure, there is a direct correlation between the position of the actuator and the position of the probe 20.

Figure 11:
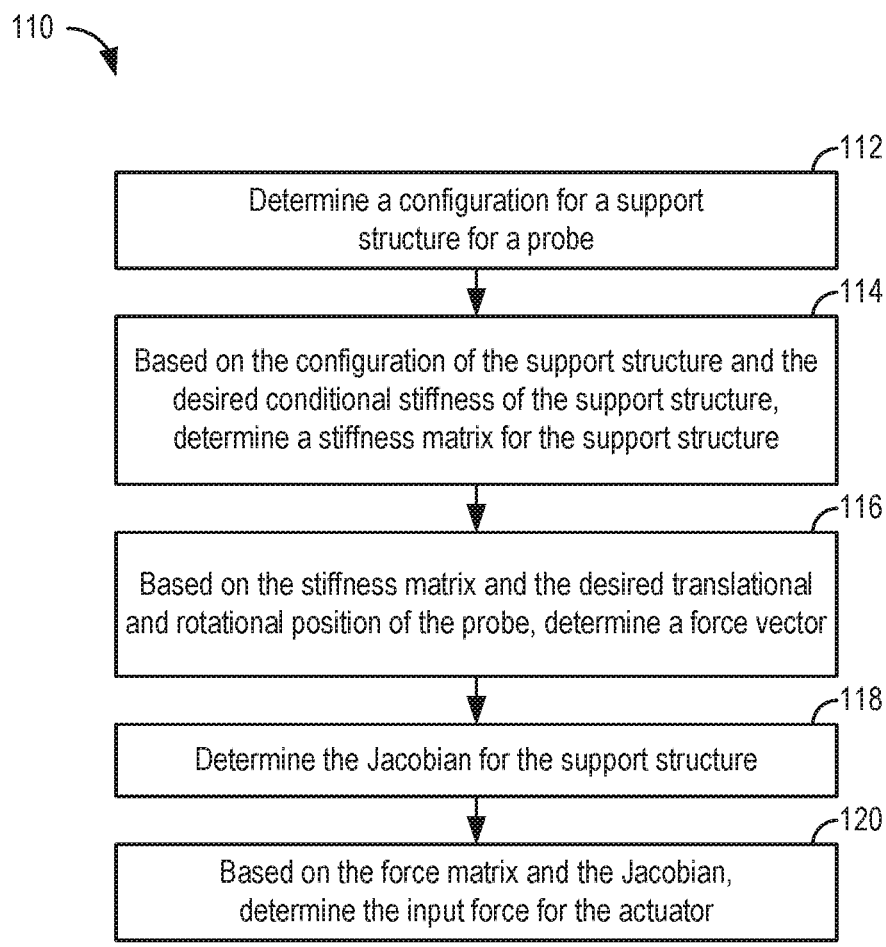
FIG. 11 is a flowchart of a method for determining the input force, or torque, for an actuator, according to an exemplary embodiment.

Referring now to FIG. 11, a method 110 of determining the input force, or torque, for an actuator for a probe support structure is shown according to an exemplary embodiment. The configuration of the support structure for a probe is first determined (step 112). The configuration may include any number of revolute joints and/or prismatic joints. In some embodiments, the support structure provides translation of the probe along one or more axis (e.g., the x, y, and z axis in a Cartesian coordinate system; the r, θ, and z axis in a polar coordinate system, etc.) and/or rotation about one or more axis.

Based on the configuration of the support structure and the desired variable stiffness of the support structure, a stiffness matrix for the support structure is determined (step 114). The stiffness matrix includes terms based on the physical properties of the support structure, including the geometry of the frame members and the stiffness of the individual frame members, the desired stiffness of the support structure in the z direction (Kz), the y direction (Ky), and the x direction (Kx), the desired rotational stiffness of the support structure ($K\omega_x$, $K\omega_y$), and a velocity-based term for system damping.

Based on the stiffness matrix and the desired translational and rotational position of the probe, a force vector is determined (step 116). The desired position of the probe may be determined using any coordinate system. According to an exemplary embodiment, the force vector is derived from the product of the stiffness matrix and a matrix of the desired translational and rotational position of the probe, as shown in Equation 1.

The Jacobian for the support structure is then calculated (step 118). The Jacobian is determined by the kinematics of the specific support structure. The Jacobian is the differential relationship between the joint positions and the end-effector position. The joint positions are either in units of radians (e.g., for rotational joints), or in units of length (e.g., for prismatic or linear joints). The Jacobian is not static and changes as the support structure position articulates.

Based on the force vector and the Jacobian, the input force for the actuator is determined (step 120). According to an exemplary embodiment, the input force for the actuator is derived from the product of the Jacobian and the force vector, as shown in Equation 2.

Figure 12:
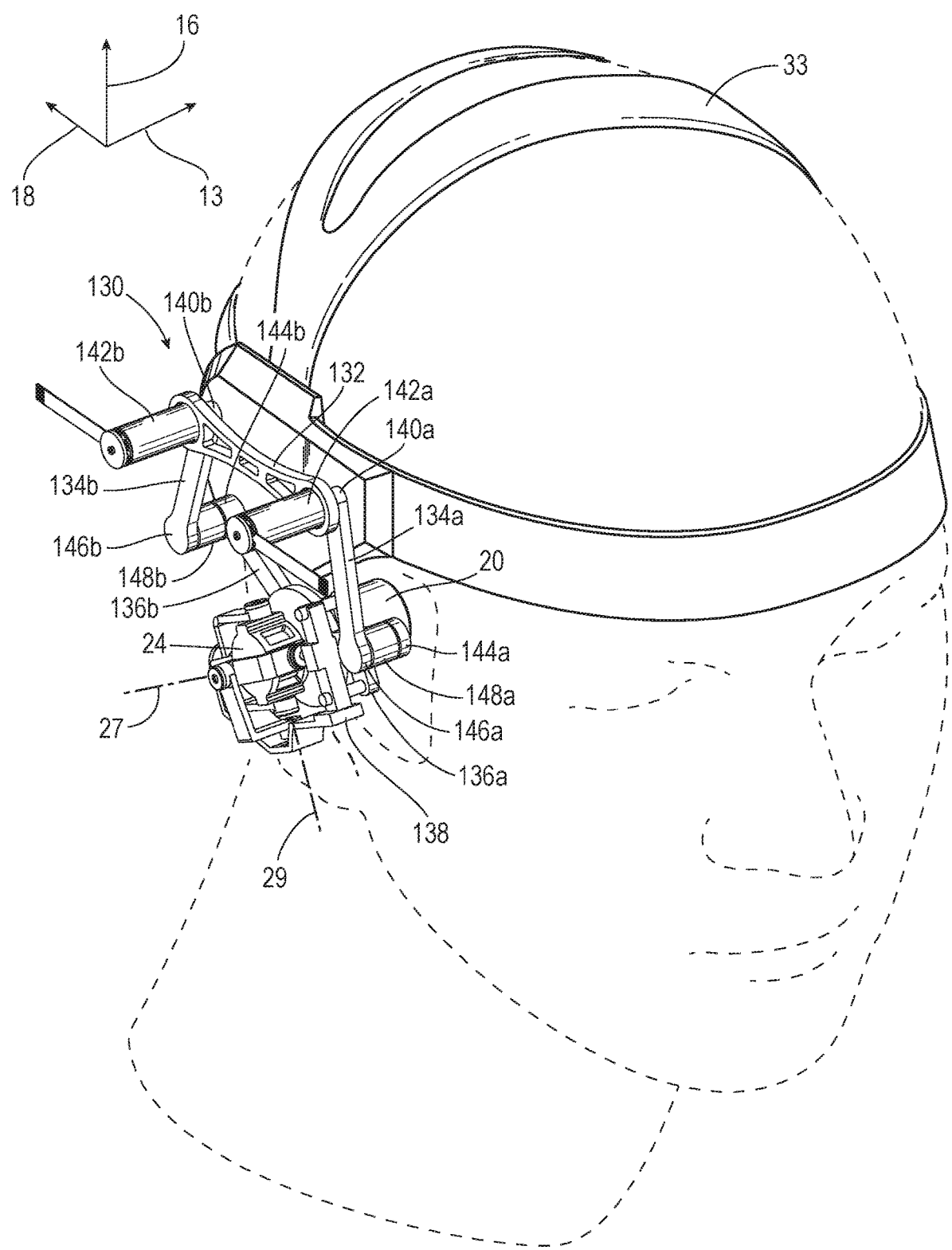
FIG. 12 is a perspective view of a 5-bar parallel mechanism (revolute-revolute) support structure for the medical probe of FIG. 2, according to an exemplary embodiment.
Figure 13:
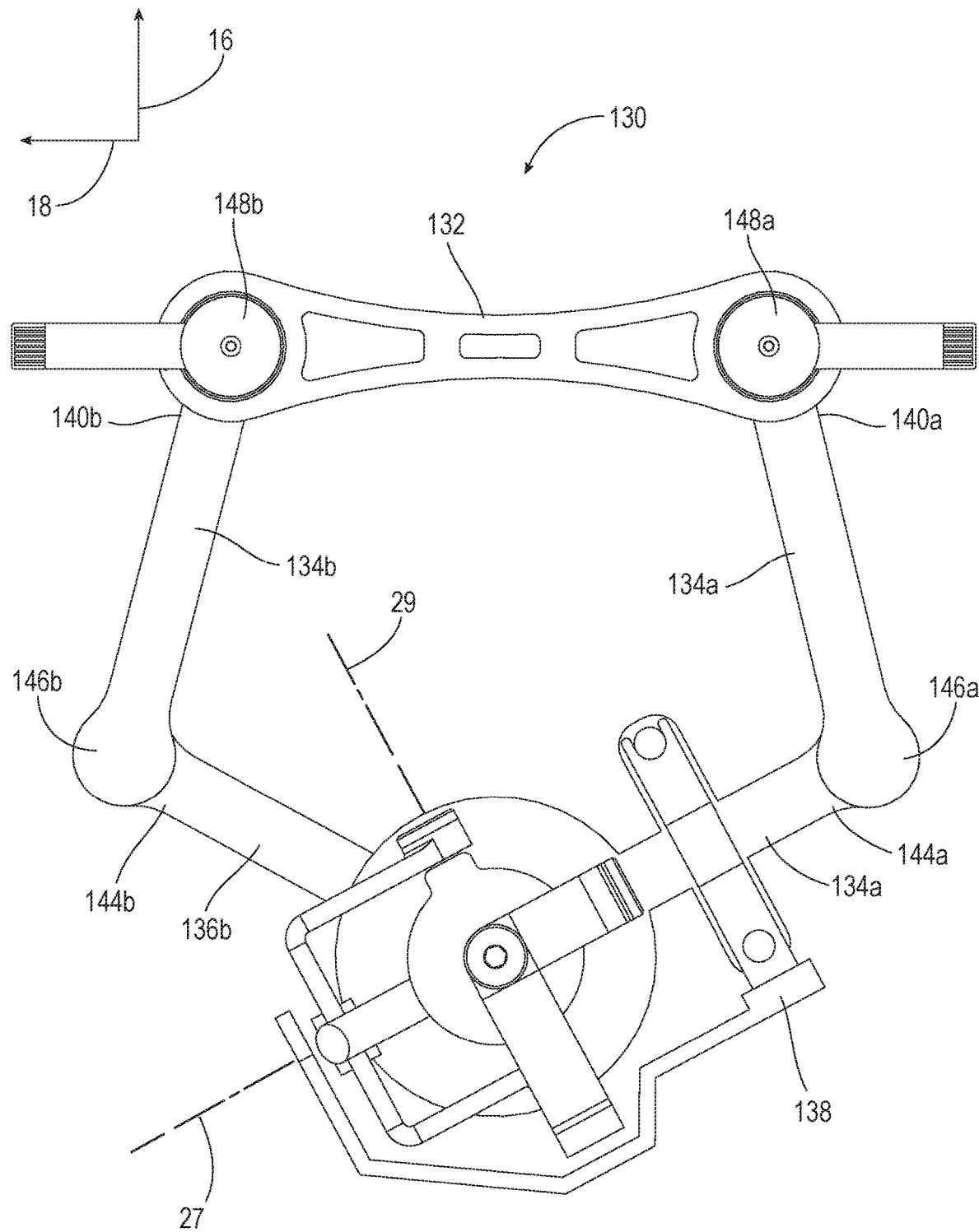
FIG. 13 is front elevation view of the support structure of FIG. 12.
Figure 14:
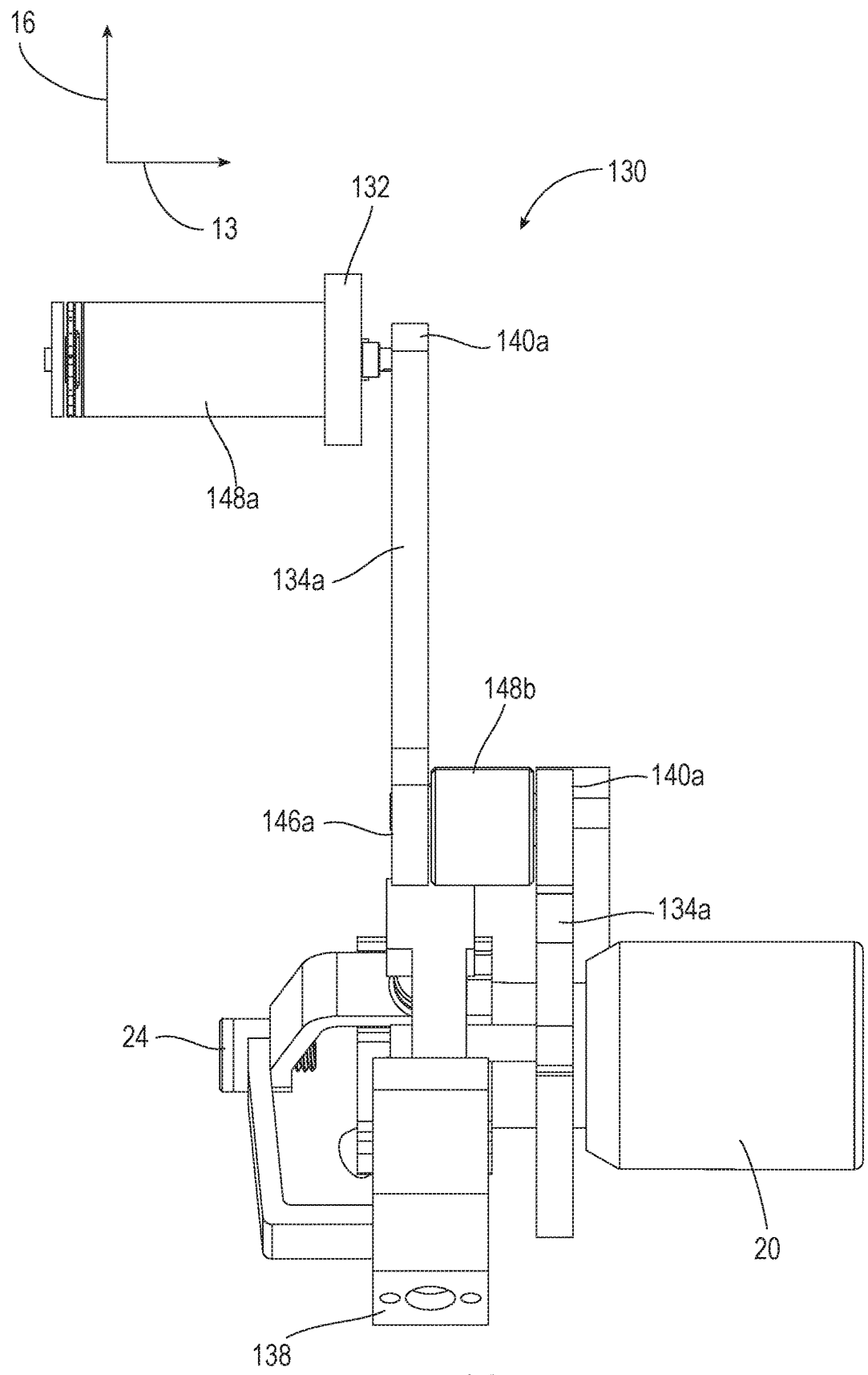
FIG. 14 is a right side elevation view of the support structure of FIG. 12.

Referring now to FIGS. 12-14, a support structure 130 for the probe 20 is shown according to another exemplary embodiment as a five-link revolute robot. The support structure 130 includes a first frame member 132; a pair of proximal members coupled to the first frame member 132, shown as a second frame member 134*a* and a third frame member 134*b*; a pair of distal members coupled to the respective proximal frame members and to each other, shown as a fourth frame member 136*a* and a fifth frame member 136*b*; a sixth frame member 138 coupled to the distal frame members; and the gimbal structure 24. The first frame member 132 is configured to be a static member. The first frame member 132 may, for example, be mounted to a halo or headset 33 worn on the patient's head or other structure that fixes the position of the first frame member 132 relative to the patient.

The second frame member 134a and the third frame member 134b are links configured to rotate about the z-axis 13. A first end 140a of the second frame member 134a is coupled to the first frame member 132. Similarly, a first end 140b of the third frame member 134b is coupled to a separate portion of the first frame member 132. According to an exemplary embodiment, the rotation of the second frame member 134a relative to the first frame member 132 is controlled by an actuator 142a, shown as an electric motor and gearbox that is attached through the first frame member 132. According to an exemplary embodiment, the rotation of the third frame member 134b relative to the first frame member 132 is controlled by an actuator 142b, shown as an electric motor and gearbox that is attached through the first frame member 132.

The fourth frame member 136a and the fifth frame member 136b are links configured to rotate about the z-axis 13. A first end 144a of the fourth frame member 136a and a second end 146a of the second frame member 134a are each coupled to a hub member 148a via bearings (e.g., press fit bearings, etc.). Similarly, a first end 144b of the fifth frame member 136b and a second end 146b of the third frame member 134b are each coupled to a hub member 148b via bearings (e.g., press fit bearings, etc.).

The fourth frame member 136a and the fifth frame member 136b are coupled together via a bearing (e.g., a press fit bearing, etc.) to form a five-bar linkage. The hub members 148a and 148b offset the proximal members from the distal members along the z-axis 13, which allows the proximal frame members (e.g., second frame member 134a and third frame member 134b) to move freely past the distal frame members (e.g., fourth frame member 136a and fifth frame member 136b) as the links are rotated by the actuators 142a and 142b.

The gimbal structure 24 and the probe 20 are mounted to the sixth frame member 138. The sixth frame member 138 is coupled to one of the distal members (e.g., fourth frame member 136a or fifth frame member 136b) and is configured to translate the gimbal structure 24 and the probe 20 along the z-axis 13 (e.g., in and out, in and away from the head, etc.). The sixth frame member 138 may translate, for example, on rails, as described above in regards to the fourth frame member 38 of the support structure 30 (see FIGS. 3-5). The gimbal structure 24 controls the orientation of the probe 20 about the tilt axis 27 and the pan axis 29 (e.g., pan and tilt). The position of the probe 20 about the tilt axis 27 is controlled by an actuator (not shown), such as an electric motor and gearbox. The position of the probe 20 about the pan axis 29 is controlled by an actuator (not shown), such as an electric motor and gearbox. In one embodiment, the rotation of the probe 20 about the tilt axis 27 and the pan axis 29 is different than the z-axis 13, regardless of the rotation of the frame members 134 and 136.

The probe 20 is able to move on the x-y plane through the movement of the five-bar linkage formed by the first frame member 132, the second frame member 134a, the third frame member 134b, the fourth frame member 136a, and the fifth frame member 136b. The probe 20 is able to move along the z-axis 13 through the translation of the sixth frame member 138. Further, the probe 20 is able to rotate about tilt axis 27 and the pan axis 29 through the gimbal structure 24. Combining these five degrees of freedom allows the position and orientation of the probe 20 relative to the target surface 22 (See FIGS. 1-2) to be completely described and con-trolled, discounting rotation about a third axis that is orthogonal to the pan axis 29 and the tilt axis 27.

According to an exemplary embodiment, the actuators utilized to position the support structure 130 are servo motors. Of course, any suitable motors could be used instead of servo motors. The use of servo motors to control the support structure allow for a more precise control, compared to a stepper motor, over the rotational position and angular speed of the motor, as well as the corresponding position of the probe 20 and the interaction between the probe 20 and the target surface 22.

The input forces for the actuators 142a and 142b can be calculated in a manner similar to that described above by determining the force vector, determining the forward kinematics of the support structure 130, and calculating the Jacobian by taking the partial derivative of the forward kinematics with respect to the rotations of each of the actuators 142a and 142b.

In some embodiments, for probe 20 contact and seating, instead of trying to predict and control the exact position and orientation of the probe 20, the impedance of the probe 20 is selectively controlled, whether by mechanical design or through software. As such, the orientation degrees of freedom of the probe 20 can be compliant so that they rotate against contact and seat the probe 20 flush with the head, while the translation degrees of freedom are stiff enough to move the probe 20 and keep it placed against the head. In some embodiments, each of the directions has different impedances.

In some embodiments, software is implemented to limit motor torque and motor servo stiffness of the probe 20. In some embodiments, there may be different limits for each direction, creating different stiffnesses in different directions. In some embodiments, the pan and tilt are very compliant, while the translational motions are moderately stiffer. In some embodiments, stiffness through the probe 20 is more compliant than the X, Y translational degrees of freedom.

In some embodiments, software is implemented for task space impedance control. In other words, there can be considered the probe 20 orientation to define a local coordinate system with the Z axis through the center of the probe 20. Instead of manipulating the impedance of the probe 20 by adjusting motor servo stiffness and torque limiting, in some embodiments, the kinematics of the entire robot can be considered to set the impedance of each of the five directions, X, Y, Z, pan, and tilt, local to the probe's 20 coordinate frame. As such, the probe 20 can be more compliant through the center line of the probe 20, but still maintain contact with the surface of the skin, but have local X and Y stiffness sufficient to control the location of the probe 20 with precision.

According to various embodiments, the probe 20 includes a series elastic actuator. In some embodiments, the impedance of the device is altered by adding a compliant member into the mechanical design, either as a spring element into the motor or as a structural member of the robot. In some embodiments, measurement of the amount of deflection is implemented in order to measure the exact position and orientation of the probe 20. A series elastic actuator has the benefit of being designed to an exact compliance, and even has a damping element added, while avoiding computational nonlinearities and instabilities associated with programming the impedance.

In some embodiments, the interaction force and torque between the probe 20 and the head is controlled by placing a force/torque sensing mechanism behind the probe 20.

Using that information the impedance of the probe 20 in software is programmed using closed loop control.

In some embodiments, the force is indirectly measured by monitoring the applied current of the motor. For the static case, taking into account the kinematics of the robot, the force/torque vector of the system is computed from the Jacobian: $F=(J^T)^{-1}\tau$, where $\tau$ is the vector of motor torques as predicted by the applied current to the motor.

While only a few configurations of a support structure for the probe 20 have been described above and shown in the figures, a person of ordinary skill in the art will understand that many other configurations are possible and that a similar methodology can be used to determine the input forces for the actuators of the support system to achieve a desired variable stiffness in any direction.

The above used terms, including "attached," "connected," "secured," and the like are used interchangeably. In addition, while certain embodiments have been described to include a first element as being "coupled" (or "attached," "connected," "fastened," etc.) to a second element, the first element may be directly coupled to the second element or may be indirectly coupled to the second element via a third element.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout the previous description that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

It is understood that the specific order or hierarchy of steps in the processes disclosed is an example of illustrative approaches. Based upon design preferences, it is understood that the specific order or hierarchy of steps in the processes may be rearranged while remaining within the scope of the previous description. The accompanying method claims present elements of the various steps in a sample order, and are not meant to be limited to the specific order or hierarchy presented.

The previous description of the disclosed implementations is provided to enable any person skilled in the art to make or use the disclosed subject matter. Various modifications to these implementations will be readily apparent to those skilled in the art, and the generic principles defined herein may be applied to other implementations without departing from the spirit or scope of the previous description. Thus, the previous description is not intended to be limited to the implementations shown herein but is to be accorded the widest scope consistent with the principles and novel features disclosed herein.

What is claimed is:

1. A headset mountable on a head, the headset comprising:
   a probe for emitting energy into the head;
   a support structure coupled to the probe, the support structure comprising:
      translation actuators configured to translate the probe along two axes parallel to a surface of the head;
      at least a perpendicular translation actuator configured to translate the probe along a perpendicular axis, wherein the perpendicular axis is perpendicular to the two axes;
      at least one rotation actuator configured to rotate the probe about a tilt axis and about a pan axis, wherein the tilt axis is orthogonal to the perpendicular axis, the pan axis is orthogonal to the perpendicular axis, and the two axes, the perpendicular axis, the tilt axis, and the pan axis are different axis;
      a first dampener exerting a force along the perpendicular axis;
      a second dampener exerting a torque about the tilt axis; and
      a third dampener exerting a torque about the pan axis.

2. The headset of claim 1, wherein the headset provides exactly five degrees of freedom of movement of the probe including translation through the two axes generally parallel to the surface of the head, one degree of freedom through the perpendicular axis generally perpendicular to the surface of the head, one degree of freedom along the tilt axis, and one degree of freedom along the pan axis.

3. The headset of claim 1, the at least one rotation actuator configured to rotate the probe about the tilt axis and about the pan axis comprises a first rotation actuator configured to rotate the probe about the tilt axis and a second rotation actuator configured to rotate the probe about the pan axis.

4. The headset of claim 3, wherein
   the first rotation actuator comprises a first motor mounted on the support structure; and
   the second rotation actuator comprises a second motor mounted on the support structure.

5. The headset of claim 1, wherein the pan axis, the tilt axis, and the perpendicular axis are orthogonal to each other.

6. The headset of claim 1, wherein
   the two axes define a translation plane parallel to the surface of the head;
   the support structure has a first stiffness along the translation plane;
   the support structure has a second stiffness along the perpendicular axis;
   the first stiffness and the second stiffness are different.

7. The headset of claim 6, wherein the first stiffness is greater than the second stiffness.

8. A device configured to interact with a target surface, the device comprising:
   a probe configured to interact with the target surface; and
   a support structure coupled to the probe for moving the probe relative to the target surface, the support structure comprising:
      translation actuators configured to translate the probe along two axes parallel to a surface of the head;
      at least a perpendicular translation actuator configured to translate the probe along a perpendicular axis, wherein the perpendicular axis is perpendicular to the two axes;
      at least one rotation actuator configured to rotate the probe about a tilt axis and about a pan axis, wherein the tilt axis is orthogonal to the perpendicular axis, the pan axis is orthogonal to the perpendicular axis, and the two axes, the perpendicular axis, the tilt axis, and the pan axis are different axis;
a first dampener exerting a force along the perpendicular axis;
a second dampener exerting a torque about the tilt axis; and
a third dampener exerting a torque about the pan axis.

9. The device of claim 8, wherein an input force of each of the translation actuators, the perpendicular translator, and the at least one rotation actuator is determined by a method comprising:
determining a configuration of the support structure for the probe and each of the translation actuators, the perpendicular translator, and the at least one rotation actuator for the support structure;
determining a stiffness matrix for the support structure based on the configuration of the support structure and a desired conditional stiffness of the support structure;
determining a force vector by multiplying the stiffness matrix and a vector of a difference of the desired and actual translational and rotational position of the probe;
calculating a Jacobian for the support structure; and
determining the input forces for each of the translation actuators, the perpendicular translator, and the at least one rotation actuator by multiplying the force vector and a transpose of the Jacobian.

10. The device of claim 8, wherein
the two axes define a translation plane parallel to the surface of the head;
the support structure has a first stiffness along the translation plane;
the support structure has a second stiffness along the perpendicular axis;
the first stiffness and the second stiffness are different.

11. The device of claim 10, wherein the first stiffness is greater than the second stiffness.

12. The device of claim 8, wherein the headset provides exactly five degrees of freedom of movement of the probe including translation through the two axes generally parallel to the surface of the head, one degree of freedom through the perpendicular axis generally perpendicular to the surface of the head, one degree of freedom along the tilt axis, and one degree of freedom along the pan axis.

13. A method of manufacturing a device configured to interact with a target surface, the method comprising:
providing a probe configured to interact with the target surface; and
coupling a support structure to the probe for moving the probe relative to the target surface, the support structure comprising:
translation actuators configured to translate the probe along two axes parallel to a surface of the head;
at least a perpendicular translation actuator configured to translate the probe along a perpendicular axis, wherein the perpendicular axis is perpendicular to the two axes;
at least one rotation actuator configured to rotate the probe about a tilt axis and about a pan axis, wherein the tilt axis is orthogonal to the perpendicular axis, the pan axis is orthogonal to the perpendicular axis, and the two axes, the perpendicular axis, the tilt axis, and the pan axis are different axis;
a first dampener exerting a force along the perpendicular axis;
a second dampener exerting a torque about the tilt axis; and
a third dampener exerting a torque about the pan axis.

14. The method of claim 13, wherein
the two axes define a translation plane parallel to the surface of the head;
the support structure has a first stiffness along the translation plane;
the support structure has a second stiffness along the perpendicular axis;
the first stiffness and the second stiffness are different.

15. The method of claim 14, wherein the first stiffness is greater than the second stiffness.

16. The method of claim 13, wherein the headset provides exactly five degrees of freedom of movement of the probe including translation through the two axes generally parallel to the surface of the head, one degree of freedom through the perpendicular axis generally perpendicular to the surface of the head, one degree of freedom along the tilt axis, and one degree of freedom along the pan axis.

17. A headset mountable on a head, the headset comprising:
a probe for emitting energy into the head;
a support structure coupled to the probe, the support structure comprising:
translation actuators configured to translate the probe along two axes parallel to a surface of the head;
at least a perpendicular translation actuator configured to translate the probe along a perpendicular axis, wherein the perpendicular axis is perpendicular to the two axes;
at least one rotation actuator configured to rotate the probe about a tilt axis and about a pan axis,
wherein the tilt axis is orthogonal to the perpendicular axis, the pan axis is orthogonal to the perpendicular axis, and the two axes, the perpendicular axis, the tilt axis, and the pan axis are different axis, wherein
the two axes define a translation plane parallel to the surface of the head;
the support structure has a first stiffness along the translation plane;
the support structure has a second stiffness along the perpendicular axis;
the first stiffness and the second stiffness are different.

18. The headset of claim 17, wherein the first stiffness is greater than the second stiffness.

19. The headset of claim 17, wherein the support structure comprises:
a first dampener exerting a force along the perpendicular axis;
a second dampener exerting a torque about the tilt axis; and
a third dampener exerting a torque about the pan axis.

20. The headset of claim 17, wherein the headset provides exactly five degrees of freedom of movement of the probe including translation through the two axes generally parallel to the surface of the head, one degree of freedom through the perpendicular axis generally perpendicular to the surface of the head, one degree of freedom along the tilt axis, and one degree of freedom along the pan axis.

* * * * *